United States Patent
Zhou et al.

(10) Patent No.: US 9,328,111 B2
(45) Date of Patent: May 3, 2016

(54) SUBSTITUTED CYCLOOCTA[5,6]PYRIDO [4,3,2-DE]PHTHALAZINES AS PARP INHIBITORS

(75) Inventors: Changyou Zhou, Princeton, NJ (US); Bo Ren, Beijing (CN); Hexiang Wang, Beijing (CN)

(73) Assignee: BeiGene Ltd., Grand Cayman (KY)

( * ) Notice: Subject to any disclaimer, the term of this patent is extended or adjusted under 35 U.S.C. 154(b) by 0 days.

(21) Appl. No.: 14/369,388

(22) PCT Filed: Dec. 31, 2011

(86) PCT No.: PCT/CN2011/085155
§ 371 (c)(1),
(2), (4) Date: Jun. 27, 2014

(87) PCT Pub. No.: WO2013/097226
PCT Pub. Date: Jul. 4, 2013

(65) Prior Publication Data
US 2015/0018356 A1    Jan. 15, 2015

(51) Int. Cl.
| | | |
|---|---|---|
| *A61K 31/5025* | (2006.01) | |
| *C07D 237/26* | (2006.01) | |
| *C07D 471/14* | (2006.01) | |
| *C07D 471/06* | (2006.01) | |
| *C07D 471/16* | (2006.01) | |
| *C07D 471/04* | (2006.01) | |

(52) U.S. Cl.
CPC ............ *C07D 471/14* (2013.01); *C07D 471/04* (2013.01); *C07D 471/06* (2013.01); *C07D 471/16* (2013.01)

(58) Field of Classification Search
CPC .......................... A61K 31/5025; C07D 237/26
USPC .......................................... 514/248; 544/233
See application file for complete search history.

(56) References Cited

FOREIGN PATENT DOCUMENTS

| JP | 2001-302669 A | 10/2001 |
|---|---|---|
| WO | WO 99/11645 | 3/1999 |
| WO | WO 2004/105700 | 12/2004 |
| WO | WO 2010/017055 | 2/2010 |
| WO | WO 2013/097226 | * 7/2013 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Jordan, V. C. Nature Reviews: Drug Discovery, 2, 2003, 205.*
Hackam, et al. JAMA, 296(14), 2006, 1731-1732.*
Stefanska, B. et al., "2,7-Dihydro-3H-pyridazino[5,4,3-kl]acridin-3-one derivatives, novel type of cytotoxic agents active on multidrug-resistant cell lines. Synthesis and biological evaluation.," Bioorganic & Medicinal Chemistry, 13(6):1969-1975 (2005).
International Preliminary Report on Patentability for International Application No. PCT/CN2011/085155, dated Jul. 1, 2014, 6 pages.
International Search Report and Written Opinion for International Application No. PCT/CN2011/085155, mailed Oct. 4, 2012, 12 pages.

* cited by examiner

*Primary Examiner* — Douglas M Willis
(74) *Attorney, Agent, or Firm* — Cooley, LLP

(57) ABSTRACT

The present invention provides a compound of Formula (I):

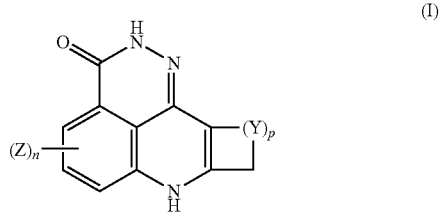

wherein the variables Z, n, Y and p are as defined herein, and pharmaceutically acceptable salts thereof, which can inhibit the activity of poly (ADP-ribose)polymerases, and pharmaceutical compositions comprising the same.

6 Claims, No Drawings

SUBSTITUTED CYCLOOCTA[5,6]PYRIDO[4,3,2-DE]PHTHALAZINES AS PARP INHIBITORS

This application is a U.S. national stage application of International Application No. PCT/CN2011/085155, which was filed on Dec. 31, 2011 with the title "FUSED TETRA OR PENTA-CYCLIC PYRIDOPHTHALAZINONES AS PARP INHIBITORS".

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

Disclosed herein are fused tetra or penta-cyclic compounds which can inhibit the activity of poly (ADP-ribose)polymerases (PARPs), pharmaceutical compositions comprising at least one of the compounds, and the use thereof in treating certain diseases.

2. Description of Related Art

Poly(ADP-ribose) polymerases (PARPs), previously known as poly(ADP-ribose) synthases or poly(ADP-ribose) transferases, are a family of proteins that contain PARP catalytic domain (*BMC Genomics,* 2005 Oct. 4; 6: 139). Approximately 17 members of PARPs have been discovered so far, including PARP-1, PARP-2, PARP-3, PARP-4 (Vault-PARP), PARP-5a (Tankyrase-1), PARP5b (Tankyrase-2), PARP-6, PARP-7 (tiPARP), PARP-8, PARP-9 (BAL1), PARP-10, PARP-11, PARP-12, PARP-13 (ZAP), PARP-14 (CoaSt6), PARP-15, and PARP-16. The catalytic activity of PARPs can be to transfer the ADP-ribose moiety from nicotinamide adenine dinucleotide ($NAD^+$) to glutamic acid residues of a number of target proteins, and to form long branches of ADP-ribose polymers. However, some of the PARP families have been reported to catalyze only mono-ADP-ribosylation of targets while activities of others have yet to be reported (*Mol. Cell.* 2008 Oct. 10; 32(1): 57-69). A number of the PARP enzymes have been reported to show important functional roles in, for example, DNA repair, transcriptional regulation, mitotic progression, genomic integrity, telomere stability, cell death, and Wnt signaling pathway.

PARP-1 may be the most abundant and most well studied member of the family, and PARP-2 may be its closest relative. PARP can be activated by damaged DNA fragments and, once activated, catalyzes the attachment of poly-ADP-ribose units to a variety of nuclear proteins, including histones and PARP itself. The resultant foci of poly(ADP-ribose) has been reported to halt transcription and recruit repair enzymes to the site of DNA damage. The pivotal role of PARP in the repair of DNA strand breaks has been reported as well established. PARP-1 knockout cells can show increased sensitivity to, for example, alkylating agents, topoisomerase (topo) I inhibitors and γ-irradiation. PARP inhibitors have been reported to sensitize tumor cells to radiation treatment (including ionizing radiation and other DNA damaging treatments) and anticancer drugs (including platinum drugs, temozolomide, and topoisomerase I inhibitors). PARP inhibitors have also been reported to be effective in radiosensitizing (hypoxic) tumor cells and in preventing tumor cells from recovering from potentially lethal and sublethal damages of DNA after radiation therapy, presumably by their ability to prevent broken DNA strand from rejoining and by affecting several DNA damage signaling pathways.

PARP inhibitors have been suggested to effectively destroy tumors defective in the BRCA1 or BRCA2 genes through the concept of synthetic lethality. While tumors with wild type BRCA genes can be insensitive to PARP inhibitors, the presence of BRCA1 or BRCA2 deficiency leads to significantly increased sensitivity of those genes to PARP inhibitors. It can be suggested that PARP inhibitors may cause an increase in DNA single-strand breaks (SSBs), which are converted during replication to toxic DNA double-strand breaks (DSBs) that cannot be repaired by homology recombination repair in BRCA1/2 defective cells. The synthetic lethality may have also been reported for PARP inhibitors, and ATM, ATR, RAD51 deficiency, and other homology recombination repair defects. PARP inhibitors can be useful for treatment of cancers with DNA repair deficiencies.

Activation of PARP may also have a role in mediating cell death. Excessive activation of PARP may have been indicated in ischemia-reperfusion injuries, and in neurological injuries that can occur during stroke, trauma and Parkinson's disease. The overactivation of PARP may lead to rapid consumption of $NAD^+$ to form ADP-ribose polymers. Because the biosynthesis of $NAD^+$ can be an ATP consuming process, the cellular level of ATP could be subsequently depleted and the ischemic cells could die from necrosis. Inhibition of PARP can be expected to reduce cell death by preserving cellular $NAD^+$ and ATP level and by preventing the activation of certain inflammation pathways that could have contributed to further cellular damage via an immune response.

It has been reported that PARP activation can play a key role in both NMDA- and NO-induced neurotoxicity. The reports were based on cortical cultures and hippocampal slices wherein prevention of toxicity can be directly correlated with PARP inhibition potency. The potential role of PARP inhibitors in treating neurodegenerative diseases and head trauma has been hypothesized.

Studies have reported that PARP inhibitors can be used for treatment and prevention of autoimmune disease such as Type I diabetes and diabetic complications (*Pharmaceutical Research* (2005)52: 60-71).

PARP-3 appears to be a newly characterized member of the PARP family. A recent study has reported the role of PARP-3 in genome integrity and mitotic progression (*PNAS*|Feb. 15, 2011|vol. 108|no. 7|2783-2788). PARP-3 deficiency can lead to reduced cellular response to DNA double-strand breaks. PARP-3 deficiency when combined with PARP-1/2 inhibitors can result in lowered cell survival in response to x-irradiation. PARP-3 can be required for mitotic spindle integrity during mitosis and telomere stability. Therefore inhibition of PARP-3 can also potentially lead to antitumor activity.

Tankyrase-1 (TRF1-interacting ankyrin-related ADP-ribosepolymerase 1) is initially identified as a component of the human telomeric complex. Tankyrase-2 may share overall sequence identity of 83% and sequence similarity of 90% with Tankyrase-1. Mouse genetic studies reportedly suggest substantial functional overlaps between tankyrase-1 and tankyrase-2. Tankyrase-1 has reportedly been shown to be a positive regulator of telomere length, allowing elongation of the telomeres by telomerase Inhibition of tankyrases can sensitize cells to telomerase inhibitors. Tankyrase-1 can be also required for sister telomere dissociation during mitosis. Inhibition of Tankyrase-1 by RNAi can induce mitotic arrest. Inhibition of tankyrases potentially may lead to antitumor activity.

Tankyrases have reportedly been implicated in the regulation of Wnt pathway. Wnt pathway can be negatively regulated by proteolysis of the downstream effector β-catenin by the β-catenin destruction complex, comprising adenomatous polyposis coli (APC), axin and glycogen synthase kinase 3α/β (GSK3α/β). Inappropriate activation of the Wnt pathway has been reported in many cancers. Notably, truncating mutations of the tumor suppressor APC can be the most prevalent genetic alterations in colorectal carcinomas. APC mutation may lead to defective β-catenin destruction complex, accumulation of nuclear β-catenin, and/or active transcription of Wnt pathway-responsive genes. Tankyrase inhibitors have been reported to stabilize the β-catenin destruction complex by increasing axin levels. Axin, a key component of β-catenin destruction complex, can be degraded through PARylation and ubiquitination. Inhibition of tankyrases can lead to reduced degradation of axin and/or increased level of axin. Tankyrase inhibitors have been reported to inhibit colony formation by APC-deficient colon cancer cells. Therefore, tankyrase inhibitors can be potentially useful for treatment of cancers with activated Wnt pathways.

Provided herein are compounds and/or pharmaceutically acceptable salts thereof, pharmaceutical compositions comprising at least one of those compounds and pharmaceutically acceptable salts thereof, and use thereof in inhibiting PARP activity for treating diseases, such as cancer For example, the compounds and compositions as described herein can be useful in treating cancers with defective DNA repair pathways, and/or can be useful in enhancing the effectiveness of chemotherapy and radiotherapy.

Certain small molecules have been reported to be PARP inhibitors. For example, PCT Publication Nos. WO 2000/42040 and 2004/800713 report tricyclic indole derivatives as PARP inhibitors. PCT Publication Nos. WO 2002/44183 and 2004/105700 report tricyclic diazepinoindole derivatives as PARP inhibitors; PCT Publication No. WO 2011/130661 and GB patent 2462361 report dihydropyridophthalazinone derivatives as PARP inhibitors; other cyclic compounds reported as PARP inhibitors can be found in the following patents: U.S. Pat. No. 7,915,280; U.S. Pat. No. 7,235,557; USRE041150; U.S. Pat. No. 6,887,996; and EP1339402B1.

PCT Publication No. WO 2004/4014294, published on Feb. 19, 2004 reports 4,7-disubstituted indole derivatives as PARP inhibitors. Other cyclic compounds as PARP inhibitors are also reported in U.S. Pat. No. 6,906,096. PCT Publication No. WO 2009/063244, published on May 22, 2009, discloses pyridazinone derivatives as PARP inhibitors. GB Patent No. 2462361, published on Oct. 2, 2010 discloses dihydropyridophthalazinone derivatives as PARP inhibitors. U.S. Pat. No. 7,429,578, published on Sep. 30, 2008, reports tricyclic derivatives as PARP inhibitors. Other cyclic compounds as PARP inhibitors are also reported in the following patents: EP1140936B1; U.S. Pat. No. 6,495,541; U.S. Pat. No. 6,799,298. U.S. Pat. No. 6,423,705, published on Jul. 23, 2003, reports a combination therapy using PARP inhibitors. Other combination therapies using PARP inhibitors are also reported in the following patent publications: US 2009/0312280A1; WO 2007113647A1. U.S. Pat. No. 6,967,198, published on Nov. 22, 2005, reports tricyclic compounds as protein kinase inhibitors for enhancing efficacy of antineoplastic agents and radiation therapy. U.S. Pat. No. 7,462,713, published on Dec. 9, 2008, also reports tricyclic compounds as protein kinase inhibitors for enhancing efficacy of antineoplastic agents and radiation therapy. EP patent No. 1585749, published on Aug. 13, 2008, reports diazepinoindole derivatives as antineoplastic agents and radiation therapy.

BRIEF SUMMARY OF THE INVENTION

Disclosed herein are compounds that can be poly(ADP-ribosyl)transferase (PARPs) inhibitors, and can be useful, for example, in treating cancers, stoke, head trauma, and neurodegenerative diseases As cancer therapeutics, the compounds/pharmaceutically acceptable salts as described herein may be used in combination with DNA-damaging cytotoxic agents, for example, cisplatin, topotecan, irinotecan, or temozolomide, and/or radiation.

Provided is at least one compound selected from compounds of Formula (I):

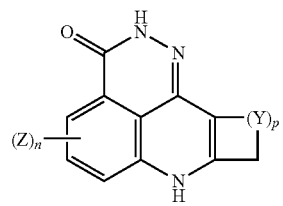

and pharmaceutically acceptable salts thereof,
wherein:
Y, at each occurrence, is independently selected from —$CR^1R^2$—, —$R^3C$=$CR^4$—, —$NR^5$—, —O—, and —S—;
p is an integer ranging from 2 to 12, such as from 2 to 5, further such as from 2 to 4, for example, p is an integer of 2 or 3;
Z, at each occurrence, is independently selected from hydrogen, halogen, alkyl, alkenyl, alkynyl, cycloalkyl, aryl, heterocyclyl, heteroaryl, —CN, —$NO_2$, —$OR^6$, —$NR^6R^7$, —$NR^6COR^7$, —$NR^6$—$NR^7COR^8$, —$NR^6SO_2R^7$, —$CONR^6R^7$, —$COOR^6$, and —$SO_2R^6$, wherein each of the alkyl, alkenyl, alkynyl, cycloalkyl, heteroaryl, aryl, and heterocyclyl is optionally substituted with at least one substituent $R^9$;
n is an integer ranging from 0 to 3, such as from 0 to 2, for example, n is an integer of 0 or 1;
$R^1$ and $R^2$, which may be the same or different, are each selected from hydrogen, halogen, alkyl, alkenyl, alkynyl, cycloalkyl, aryl, heterocyclyl, heteroaryl, —$NR^6R^7$, —$OR^6$, —$COR^6$, —$CO_2R^6$, —$CONR^6R^7$, —$NR^6CONR^7R^8$, —$NR^6CO_2R^7$, —$NR^6SO_2R^7$, and —$SO_2R^6$, wherein each of the alkyl, alkenyl, alkynyl, cycloalkyl, heteroaryl, aryl, and heterocyclyl is optionally substituted with at least one substituent $R^9$; and when $(Y)_p$ comprises —$CR^1R^2$—$CR^1R^2$—, optionally $R^1$ or $R^2$ substituted on each of the two carbons, together with the two carbons to which they are attached, form a 3- to 8-membered ring optionally substituted with at least one substituent $R^9$, wherein said ring is saturated or partially unsaturated having 0, 1 or 2 heteroatoms independently selected from —NR$^{10}$—, —O—, —S—, —SO— and —SO$_2$—;

R$^3$ and R$^4$, which may be the same or different, are each selected from hydrogen and alkyl, or R$^3$ and R$^4$, together with the carbons to which they are attached, form a 5-, 6-, 7-, or, 8-membered ring optionally substituted with at least one substituent R$^9$, wherein said ring is partially or fully unsaturated having 0, 1 or 2 heteroatoms independently selected from —NR$^{10}$—, —O—, —S—, —SO— and —SO$_2$—;

R$^5$, at each occurrence, is independently selected from hydrogen, alkyl, alkenyl, alkynyl, cycloalkyl, aryl, heterocyclyl, heteroaryl, —COR$^6$, —CO$_2$R$^6$, —CONR$^6$R$^7$, SO$_2$NR$^6$R$^7$ and —SO$_2$R$^6$, wherein each of the alkyl, alkenyl, alkynyl, cycloalkyl, heteroaryl, aryl, and heterocyclyl is optionally substituted by at least one substituent R$^9$;

R$^6$, R$^7$ and R$^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent R$^9$;

R$^9$, at each occurrence, is independently selected from halogen, haloalkyl, alkyl, alkenyl, cycloalkyl, aryl, heteroaryl, heterocyclyl, alkynyl, oxo, —CN, —OR', —NR'R", —COR', —CO$_2$R', —CONR'R", —C(=NR')NR"R'", —NR'COR", —NR'CONR'R", —NR'CO$_2$R", —SR', —SOR', —SO$_2$R', —NR'SO$_2$NR"R'", and NR'SO$_2$R", wherein R', R", and R'" are independently selected from hydrogen, haloalkyl, alkyl, arylalkyl, alkenyl, alkynyl, cycloalkyl, heterocyclyl, aryl, and heteroaryl; and R$^{10}$ is selected from hydrogen, alkyl, cycloalkyl, aryl, heteroaryl, and heterocyclyl.

Also provided is a pharmaceutical composition comprising at least one pharmaceutically acceptable carrier and at least one compound selected from compounds of Formula (I) and pharmaceutically acceptable salts thereof as described herein.

Also provided is a method of inhibiting PARP comprising contacting the PARP with an amount of at least one compound selected from compounds of Formula (I) and pharmaceutically acceptable salts thereof as described herein effective to inhibit the PARP.

Also provided is a method of treating at least one disease responsive to inhibition of PARP comprising administering to a subject in recognized need of such treating for the at least one disease an amount of at least one compound selected from compounds of Formula (I) and pharmaceutically acceptable salts thereof as described herein effective to treat the at least one disease, wherein the at least one disease is selected from, for example, cancer (such as leukemia, colon cancer, glioblastomas, lymphomas, melanomas, carcinomas of the breast, and cervical carcinomas), cytotoxic cancer, ischemia reperfusion injury (such as those associated with, but not limited to, heart failure, myocardial infarction, stroke, other neural trauma, and organ transplantation), reperfusion (such as the reperfusion of the eye, kidney, gut and skeletal muscle), inflammatory diseases (such as arthritis, gout, inflammatory bowel disease, CNS inflammation, multiple sclerosis, allergic encephalitis, sepsis, septic shock, hemmorhagic shock, pulmonary fibrosis, and uveitis), immunological diseases or disorders (such as rheumatoid arthritis and septic shock), degenerative disease (such as diabetes and Parkinsons disease), hypoglycemia, retroviral infection, liver toxicity following acetominophen overdose, cardiac and kidney toxicities from doxorubicin and platinum based antineoplastic agents, skin damage secondary to sulfur mustards.

Also provided is a use of at least one compound selected from compounds of Formula (I) and pharmaceutically acceptable salts thereof as described herein in manufacture of a medicament for inhibiting PARP.

Also provided is a use of at least one compound selected from compounds of Formula (I) and pharmaceutically acceptable salts thereof as described herein in the manufacture of a medicament for treating at least one disease selected from, for example, cancer (such as leukemia, colon cancer, glioblastomas, lymphomas, melanomas, carcinomas of the breast, and cervical carcinomas), cytotoxic cancer, ischemia reperfusion injury (such as those associated with, but not limited to, heart failure, myocardial infarction, stroke, other neural trauma, and organ transplantation), reperfusion (such as the reperfusion of the eye, kidney, gut and skeletal muscle), inflammatory diseases (such as arthritis, gout, inflammatory bowel disease, CNS inflammation, multiple sclerosis, allergic encephalitis, sepsis, septic shock, hemmorhagic shock, pulmonary fibrosis, and uveitis), immunological diseases or disorders (such as rheumatoid arthritis and septic shock), degenerative disease (such as diabetes and Parkinsons disease), hypoglycemia, retroviral infection, liver toxicity following acetominophen overdose, cardiac and kidney toxicities from doxorubicin and platinum based antineoplastic agents, skin damage secondary to sulfur mustards.

DETAILED DESCRIPTION OF THE INVENTION

As used herein, the following words, phrases and symbols are generally intended to have the meanings as set forth below, except to the extent that the context in which they are used indicates otherwise. The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 6, carbon atoms. Examples of the alkyl group can be selected from methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$) and 3,3-dimethyl-2-butyl (—CH(CH$_3$)C(CH$_3$)$_3$ groups.

The term "alkenyl" herein refers to a hydrocarbon group selected from linear and branched hydrocarbon groups comprising at least one C=C double bond and from 2 to 18, such as from 2 to 6, carbon atoms. Examples of the alkenyl group may be selected from ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as from 2 to 6, carbon atoms. Examples of the alkynyl group include ethynyl (—C≡CH), 1-propynyl (—C≡CCH$_3$), 2-propynyl (propargyl, —CH$_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo [2.2.1]heptane, bicyclo[2.2.2]octane, and bicyclo[3.2.2] nonane. The ring may be saturated or have at least one double bond (i.e. partially unsaturated), but is not fully conjugated, and is not aromatic, as aromatic is defined herein.

The term "Aryl" herein refers to a group selected from:
5- and 6-membered carbocyclic aromatic rings, for example, phenyl;
bicyclic ring systems such as 7 to 12 membered bicyclic ring systems wherein at least one ring is carbocyclic and aromatic, selected, for example, from naphthalene, indane, and 1,2,3,4-tetrahydroquinoline; and
tricyclic ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "arylalkyl" herein refers to an alkyl group as defined above substituted by an aryl group as defined above.

The term "halogen" or "halo" herein refers to F, Cl, Br or I.

The term "heteroaryl" herein refers to a group selected from:
5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;
8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein. Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoiosomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "pharmaceutically acceptable salts thereof" include salts of at least one compound of Formulas I, II (including II-1, II-2 or II-3) and III, and salts of the stereoisomers of at least one compound of Formulas I, II (including II-1, II-2 or II-3) and III, such as salts of enantiomers, and/or salts of diastereomers.

"Treating", "treat", or "treatment" or "alleviation" refers to administering at least one compound and/or at least one pharmaceutically acceptable salt thereof disclosed herein to a subject in recognized need thereof that has, for example, cancer and/or inflammatory disease, or has a symptom of, for example, cancer and/or inflammatory disease, or has a predisposition toward, for example, cancer and/or inflammatory disease, with the purpose to cure, heal, alleviate, relieve, alter, remedy, ameliorate, improve, or affect, for example, cancer and/or inflammatory disease, the symptoms of, for example, cancer and/or inflammatory disease, or the predisposition toward, for example, cancer and/or inflammatory disease.

The term "effective amount" refers to an amount of at least one compound and/or at least one pharmaceutically acceptable salt thereof disclosed herein effective to "treat," as defined above, a disease or disorder in a subject. In the case of cancer, the effective amount may cause any of the changes observable or measurable in a subject as described in the definition of "treating," "treat," "treatment" and "alleviation" above. For example, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of PARP. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents.

The term "inhibition" indicates a decrease in the baseline activity of a biological activity or process. "Inhibition of PARP" refers to a decrease in the activity of PARP as a direct or indirect response to the presence of at least one compound and/or at least one pharmaceutically acceptable salt disclosed herein, relative to the activity of PARP in the absence of the at least one compound and/or the at least one pharmaceutically acceptable salt thereof. The decrease in activity is not bound by theory and may be due to the direct interaction of the at least one compound and/or at least one pharmaceutically acceptable salt thereof disclosed herein with PARP, or due to the interaction of the at least one compound and/or at least one pharmaceutically acceptable salt disclosed herein, with one or more other factors that in turn affect PARP activity. For example, the presence of at least one compound and/or at least one pharmaceutically acceptable salt thereof disclosed herein, may decrease PARP activity by directly binding to the PARP, by causing (directly or indirectly) another factor to decrease PARP activity, or by (directly or indirectly) decreasing the amount of PARP present in the cell or organism.

The term "at least one substituent" disclosed herein includes, for example, from 1 to 4, such as from 1 to 3, further as 1 or 2, substituents. For example, "at least one substituent $R^9$" disclosed herein includes from 1 to 4, such as from 1 to 3, further as 1 or 2, substituents selected from the list of $R^9$ as described herein.

In the first aspect, provided is at least one compound selected from compounds of Formula (I):

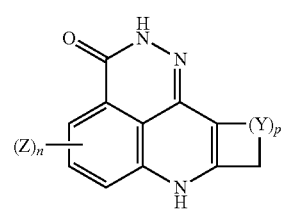

I and pharmaceutically acceptable salts thereof,
wherein:

Y, at each occurrence, is independently selected from $—CR^1R^2—$, $—R^3C=CR^4—$, $—NR^5—$, $—O—$, and $—S—$;

p is an integer ranging from 2 to 12, such as from 2 to 5, further such as from 2 to 4, for example, p is an integer of 2 or 3;

Z, at each occurrence, is independently selected from hydrogen, halogen, alkyl, alkenyl, alkynyl, cycloalkyl, aryl, heterocyclyl, heteroaryl, $—CN$, $—NO_2$, $—OR^6$, $—NR^6R^7$, $—NR^6COR^7$, $—NR^6—NR^7COR^8$, $—NR^6SO_2R^7$, $—CONR^6R^7$, $—COOR^6$, and $—SO_2R^6$, wherein each of the alkyl, alkenyl, alkynyl, cycloalkyl, heteroaryl, aryl, and heterocyclyl is optionally substituted with at least one substituent $R^9$;

n is an integer ranging from 0 to 3, such as from 0 to 2, for example, n is an integer of 0 or 1;

$R^1$ and $R^2$, which may be the same or different, are each selected from hydrogen, halogen, alkyl, alkenyl, alkynyl, cycloalkyl, aryl, heterocyclyl, heteroaryl, $—NR^6R^7$, $—OR^6$, $—COR^6$, $—CO_2R^6$, $—CONR^6R^7$, $—NR^6CONR^7R^8$, $—NR^6CO_2R^7$, $—NR^6SO_2R^7$, and $—SO_2R^6$, wherein each of the alkyl, alkenyl, alkynyl, cycloalkyl, heteroaryl, aryl, and heterocyclyl is optionally substituted with at least one substituent $R^9$; and when $(Y)_p$ comprises $—CR^1R^2—CR^1R^2—$, optionally $R^1$ or $R^2$ substituted on each of the two carbons, together with the two carbons to which they are attached, form a 3- to 8-membered ring optionally substituted with at least one substituent $R^9$, wherein said ring is saturated or partially unsaturated having 0, 1 or 2 heteroatoms independently selected from $—NR^{10}—$, $—O—$, $—S—$, $—SO—$ and $—SO_2—$;

$R^3$ and $R^4$, which may be the same or different, are each selected from hydrogen and alkyl, or $R^3$ and $R^4$, together with the carbons to which they are attached, form a 5-, 6-, 7-, or, 8-membered ring optionally substituted with at least one substituent $R^9$, wherein said ring is partially or fully unsaturated having 0, 1 or 2 heteroatoms independently selected from $—NR^{10}—$, $—O—$, $—S—$, $—SO—$ and $—SO_2—$;

$R^5$, at each occurrence, is independently selected from hydrogen, alkyl, alkenyl, alkynyl, cycloalkyl, aryl, heterocyclyl, heteroaryl, $—COR^6$, $—CO_2R^6$, $—CONR^6R^7$, $SO_2NR^6R^7$ and $—SO_2R^6$, wherein each of the alkyl, alkenyl, alkynyl, cycloalkyl, heteroaryl, aryl, and heterocyclyl is optionally substituted by at least one substituent $R^9$;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$;

$R^9$, at each occurrence, is independently selected from halogen, haloalkyl, alkyl, alkenyl, cycloalkyl, aryl, heteroaryl, heterocyclyl, alkynyl, oxo, $—CN$, $—OR'$, $—NR'R''$, —COR', —CO$_2$R', —CONR'R'', —C(=NR')NR''R''', —NR'COR'', —NR'CONR'R'', —NR'CO$_2$R'', —SR', —SOR', —SO$_2$R', —NR'SO$_2$NR''R''', and NR'SO$_2$R'', wherein R', R'', and R''' are independently selected from hydrogen, haloalkyl, alkyl, arylalkyl, alkenyl, alkynyl, cycloalkyl, heterocyclyl, aryl, and heteroaryl; and $R^{10}$ is selected from hydrogen, alkyl, cycloalkyl, aryl, heteroaryl, and heterocyclyl.

In some embodiments, Y in Formula (I), at each occurrence, is independently selected from $CR^1R^2$—, —$R^3C$=$CR^4$—, and —$NR^5$—.

In some embodiments, $R^1$ and $R^2$ in Formula (I), which may be the same or different, are each selected from hydrogen, halogen, alkyl, and aryl, wherein each of the alkyl or aryl can be optionally substituted with at least one substituent $R^9$. In some embodiments, $R^1$ and $R^2$ in Formula (I) are both hydrogen. In some embodiments, at least one pair of $R^1$ and $R^2$ in Formula (I) is alkyl (such as $C_{1-6}$ alkyl, further such as methyl).

In some embodiments, n in Formula (I) is an integer of 1. In some embodiments, Z in Formula (I) is independently selected from halogen (such as F, Cl, Br or I) and alkyl (such as $C_{1-6}$alkyl, further such as methyl).

In some embodiments, p in Formula (I) is an integer of 2; $R^1$ and $R^2$ in Formula (I), which may be the same or different, are each selected from hydrogen, halogen, alkyl (such as $C_{1-6}$ alkyl, further such as methyl), and aryl (such as phenyl); Z in Formula (I) is independently selected from halogen (such as F, Cl, Br or I) and alkyl (such as $C_{1-6}$alkyl, further such as methyl).

In some embodiments, p in Formula (I) is an integer of 3; $R^1$ and $R^2$ in Formula (I), which may be the same or different, are each selected from hydrogen, halogen, alkyl (such as $C_{1-6}$ alkyl, further such as methyl), and aryl (such as phenyl); Z in Formula (I) is independently selected from halogen (such as F, Cl, Br or I) and alkyl (such as $C_{1-6}$alkyl, further such as methyl).

In some embodiments, p in Formula (I) is an integer of 4; $R^1$ and $R^2$ in Formula (I), which may be the same or different, are each selected from hydrogen, halogen, alkyl (such as $C_{1-6}$ alkyl, further such as methyl), and aryl (such as phenyl); Z in Formula (I) is independently selected from halogen (such as F, Cl, Br or I) and alkyl (such as $C_{1-6}$alkyl, further such as methyl).

In some embodiments, p Formula (I) is an integer of 5; $R^1$ and $R^2$ in Formula (I), which may be the same or different, are each selected from the group consisting of hydrogen, halogen, alkyl (such as $C_{1-6}$ alkyl, further such as methyl), and aryl (such as phenyl); Z in Formula (I) is independently selected from halogen (such as F, Cl, Br or I) and alkyl (such as $C_{1-6}$alkyl, further such as methyl).

In some embodiments, p Formula (I) is an integer of 6, 7, 8, 9, 10, 11 or 12; $R^1$ and $R^2$ in Formula (I), which may be the same or different, are each selected from hydrogen, halogen, alkyl (such as $C_{1-6}$ alkyl, further such as methyl), and aryl (such as phenyl); Z in Formula (I) is independently selected from halogen (such as F, Cl, Br or I) and alkyl (such as $C_{1-6}$alkyl, further such as methyl).

In some embodiments, the —(Y)$_p$— moiety in Formula (I) has the structure of —$R^3C$=$CR^4$—$CH_2$—, wherein $R^3$ and $R^4$, which may be the same or different, are each selected from hydrogen and alkyl, or $R^3$ and $R^4$, together with the carbons to which they are attached, form a 5-, 6-, 7-, or, 8-membered ring optionally substituted with at least one substituent $R^9$, wherein said ring is partially or fully unsaturated having 0, 1 or 2 heteroatoms independently selected from —$NR^{10}$—, —O—, —S—, —SO—, and —SO$_2$—.

In some further embodiments, the —(Y)$_p$— moiety in Formula (I) has the structure of —$R^3C$=$CR^4$—$CH_2$—, wherein $R^3$ and $R^4$, together with the carbons to which they are attached, form a 5-, 6-, 7-, or, 8-membered ring optionally substituted with at least one substituent $R^9$, wherein said ring is partially or fully unsaturated having 0, 1 or 2 heteroatoms independently selected from —$NR^{10}$—, —O—, —S—, —SO—, and —SO$_2$—; wherein $R^9$, at each occurrence, is independently selected from halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR')NR''R''', —NR'COR'', —NR'CONR'R'', —NR'CO$_2$R'', —SR', —SOR', —SO$_2$R', —NR'SO$_2$NR''R''', and NR'SO$_2$R'', wherein R', R'', and R''' are independently selected hydrogen, haloalkyl, alkyl, arylalkyl, alkenyl, alkynyl, cycloalkyl, heterocyclyl, aryl, and heteroaryl.

In some further embodiments, —(Y)$_p$— in Formula (I) has the structure of —$R^3C$=$CR^4$—$CH_2$—, wherein $R^3$ and $R^4$, together with the carbons to which they are attached, form a 6-membered carbocyclic ring which is partially or fully unsaturated.

In the second aspect, the at least one compound selected from compounds of Formula (I) and pharmaceutically acceptable salts thereof is selected from compounds of Formula (II) below:

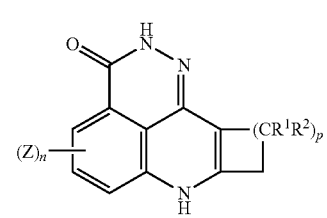

and pharmaceutically acceptable salts thereof, wherein p is an integer ranging from 2 to 12, such as from 2 to 5, further such as from 2 to 4, even further such as from 2 to 3;

Z, at each occurrence, is independently selected from hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent $R^9$;

n is an integer ranging from 0 to 3, such as from 0 to 2, further such as from 0 to 1;

$R^1$ and $R^2$, which may be the same or different, are each selected from hydrogen, halogen, alkyl, alkenyl, alkynyl, cycloalkyl, aryl, heterocyclyl, heteroaryl, —NR$^6$R$^7$, —OR$^6$, —COR$^6$, —CO$_2$R$^6$, —CONR$^6$R$^7$, —NR$^6$CONR$^7$R$^8$, —NR$^6$CO$_2$R$^7$, —NR$^6$SO$_2$R$^7$, and —SO$_2$R$^6$, wherein each of the alkyl, alkenyl, alkynyl, cycloalkyl, heteroaryl, aryl, and heterocyclyl is optionally substituted with at least one substituent $R^9$; and optionally $R^1$ or $R^2$ substituted on each of the two neighboring carbons, together with the two neighboring carbons to which they are attached, form a 3- to 8-membered ring optionally substituted with at least one substituent $R^9$, wherein said ring is saturated or partially unsaturated having 0, 1 or 2 heteroatoms independently selected from —$NR^{10}$—, —O—, —S—, —SO— and —SO$_2$—;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$;

$R^9$, at each occurrence, is independently selected from hydrogen, halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR')NR''R''', —NR'COR'', —NR'CONR'R'', —NR'CO$_2$R'', —SR', —SOR', —SO$_2$R', —NR'SO$_2$NR''R''', and NR'SO$_2$R'', wherein R', R'', and R''' are independently selected from the group consisting of H, haloalkyl, alkyl, arylalkyl, alkenyl, alkynyl, cycloalkyl, heterocyclyl, aryl, and heteroaryl; and $R^{10}$ is selected from hydrogen, alkyl, cycloalkyl, aryl, hetereoaryl, and heterocyclyl.

In some embodiments, the at least one compound selected from compounds of Formula (I) and pharmaceutically acceptable salts thereof is selected from compounds of Formula (II-1) below:

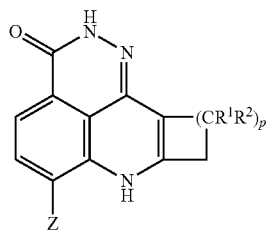

II-1 and pharmaceutically acceptable salts thereof,
wherein
p is an integer ranging from 2 to 12, such as from 2 to 5, further such as from 2 to 4, even further such as from 2 to 3;
Z, is selected from hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent $R^9$;

$R^1$ and $R^2$, which may be the same or different, are each selected from hydrogen, halogen, alkyl, alkenyl, alkynyl, cycloalkyl, aryl, heterocyclyl, heteroaryl, —NR$^6$R$^7$, —OR$^6$, —COR$^6$, —CO$_2$R$^6$, —CONR$^6$R$^7$, —NR$^6$CONR$^7$R$^8$, —NR$^6$CO$_2$R$^7$, —NR$^6$SO$_2$R$^7$, and —SO$_2$R$^6$, wherein each of the alkyl, alkenyl, alkynyl, cycloalkyl, heteroaryl, aryl, and heterocyclyl is optionally substituted with at least one substituent $R^9$; and optionally $R^1$ or $R^2$ substituted on each of the two neighboring carbons, together with the two neighboring carbons to which they are attached, form a 3- to 8-membered ring optionally substituted with at least one substituent $R^9$, wherein said ring is saturated or partially unsaturated having 0, 1 or 2 heteroatoms independently selected from —NR$^{10}$—, —O—, —S—, —SO— and —SO$_2$—;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$;

$R^9$, at each occurrence, is independently selected from hydrogen, halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR')NR''R''', —NR'COR'', —NR'CONR'R'', —NR'CO$_2$R'', —SR', —SOR', —SO$_2$R', —NR'SO$_2$NR''R''', and NR'SO$_2$R'', wherein R', R'', and R''' are independently selected from hydrogen, haloalkyl, alkyl, arylalkyl, alkenyl, alkynyl, cycloalkyl, heterocyclyl, aryl, and heteroaryl; and $R^{10}$ is selected from hydrogen, alkyl, cycloalkyl, aryl, heteroaryl, and heterocyclyl.

In some embodiments, the at least one compound selected from compounds of Formula (I) and pharmaceutically acceptable salts thereof is selected from compounds of Formula (II-2) below:

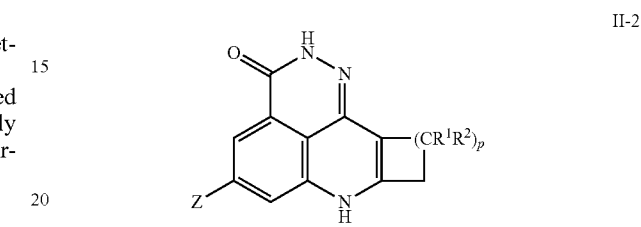

II-2 and pharmaceutically acceptable salts thereof,
wherein
p is an integer ranging from 2 to 12, such as from 2 to 5, further such as from 2 to 4, even further such as from 2 to 3;
Z is selected from hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent $R^9$;

$R^1$ and $R^2$, which may be the same or different, are each selected from hydrogen, halogen, alkyl, alkenyl, alkynyl, cycloalkyl, aryl, heterocyclyl, heteroaryl, —NR$^6$R$^7$, —OR$^6$, —COR$^6$, —CO$_2$R$^6$, —CONR$^6$R$^7$, —NR$^6$CONR$^7$R$^8$, —NR$^6$CO$_2$R$^7$, —NR$^6$SO$_2$R$^7$, and —SO$_2$R$^6$, wherein each of the alkyl, alkenyl, alkynyl, cycloalkyl, heteroaryl, aryl, and heterocyclyl is optionally substituted with at least one substituent $R^9$; and optionally $R^1$ or $R^2$ substituted on each of the two neighboring carbons, together with the two neighboring carbons to which they are attached, form a 3- to 8-membered ring optionally substituted with at least one substituent $R^9$, wherein said ring is saturated or partially unsaturated having 0, 1 or 2 heteroatoms independently selected from —NR$^{10}$—, —O—, —S—, —SO— and —SO$_2$—;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$;

$R^9$, at each occurrence, is independently selected from hydrogen, halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR')NR''R''', —NR'COR'', —NR'CONR'R'', —NR'CO$_2$R'', —SR', —SOR', —SO$_2$R', —NR'SO$_2$NR''R''', and NR'SO$_2$R'', wherein R', R'', and R''' are independently selected from hydrogen, haloalkyl, alkyl, arylalkyl, alkenyl, alkynyl, cycloalkyl, heterocyclyl, aryl, and heteroaryl; and $R^{10}$ is selected from hydrogen, alkyl, cycloalkyl, aryl, hetereoaryl, and heterocyclyl.

In some embodiments, the at least one compound selected from compounds of Formula (I) and pharmaceutically acceptable salts thereof is selected from compounds of Formula (II-3)

(II-3)

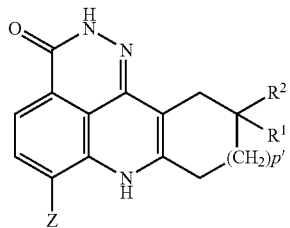

wherein p' is an integer ranging from 0-10, scuh as from 0 to 3, further such as from 0 to 2, for example, p is an integer of 0 or 1;

Z is selected from the group consisting of hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent R$^9$;

R$^1$ and R$^2$, which may be the same or different, are each selected from hydrogen, halogen, alkyl, alkenyl, alkynyl, cycloalkyl, aryl, heterocyclyl, heteroaryl, —NR$^6$R$^7$, —OR$^6$, —COR$^6$, —CO$_2$R$^6$, —CONR$^6$R$^7$, —NR$^6$CONR$^7$R$^8$, —NR$^6$CO$_2$R$^7$, —NR$^6$SO$_2$R$^7$, and —SO$_2$R$^6$, wherein each of the alkyl, alkenyl, alkynyl, cycloalkyl, heteroaryl, aryl, and heterocyclyl is optionally substituted with at least one substituent R$^9$;

R$^6$, R$^7$ and R$^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heterocyclyl is optionally substituted by at least one substituent R$^9$;

R$^9$, at each occurrence, is independently selected from hydrogen, halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR') NR''R''', —NR'COR'', —NR'CONR'R'', —NR'CO$_2$R'', —SR', —SOR', —SO$_2$R', —NR'SO$_2$NR''R''', and NR'SO$_2$R'', wherein R', R'', and R''' are independently selected from hydrogen, haloalkyl, alkyl, arylalkyl, alkenyl, alkynyl, cycloalkyl, aryl, and heteroaryl; and R$^{10}$ is selected from hydrogen, alkyl, cycloalkyl, aryl, heteroaryl, and heterocyclyl.

In some embodiments, R$^1$ and R$^2$ in each of Formulas (II), (II-1), (II-2) and (II-3), which may be the same or different, are each selected from hydrogen, halogen, alkyl, and aryl, wherein each of the alkyl or aryl can be optionally substituted with at least one substituent R$^9$. In some embodiments, R$^1$ and R$^2$ in each of Formulas (II), (II-1), (II-2) and (II-3) are both hydrogen. In some embodiments, at least one pair of R$^1$ and R$^2$ in each of Formulas (II), (II-1), (II-2) and (II-3) is alkyl (such as C$_{1-6}$ alkyl, further such as methyl).

In some embodiments, n in Formula (II) is an integer of 1. In some embodiments, Z in each of Formulas (II), (II-1), (II-2) and (II-3) is independently selected from halogen (such as F, Cl, Br or I) and alkyl (such as C$_{1-6}$alkyl, further such as methyl).

In some embodiments, p in each of Formulas (II), (II-1), and (II-2) is an integer of 2; and p' in Formula (II-3) is an integer of 0; R$^1$ and R$^2$ in each of Formulas (II), (II-1), (II-2) and (II-3), which may be the same or different, are each selected from hydrogen, halogen, alkyl (such as C$_{1-6}$ alkyl, further such as methyl), and aryl (such as phenyl); Z in each of Formulas (II), (II-1), (II-2) and (II-3) is independently selected from halogen (such as F, Cl, Br or I) and alkyl (such as C$_{1-6}$alkyl, further such as methyl).

In some embodiments, p in each of Formulas (II), (II-1), and (II-2) is an integer of 3; and p' in Formula (II-3) is an integer of 1; R$^1$ and R$^2$ in each of Formulas (II), (II-1), (II-2) and (II-3), which may be the same or different, are each selected from hydrogen, halogen, alkyl (such as C$_{1-6}$ alkyl, further such as methyl), and aryl (such as phenyl); Z in each of Formulas (II), (II-1), (II-2) and (II-3) is independently selected from halogen (such as F, Cl, Br or I) and alkyl (such as C$_{1-6}$alkyl, further such as methyl).

In some embodiments, p in each of Formulas (II), (II-1), and (II-2) is an integer of 4; and p' in Formula (II-3) is an integer of 2; R$^1$ and R$^2$ in each of Formulas (II), (II-1), (II-2) and (II-3), which may be the same or different, are each selected from hydrogen, halogen, alkyl (such as C$_{1-6}$ alkyl, further such as methyl), and aryl (such as phenyl); Z in each of Formulas (II), (II-1), (II-2) and (II-3) is independently selected from halogen (such as F, Cl, Br or I) and alkyl (such as C$_{1-6}$alkyl, further such as methyl).

In some embodiments, p in each of Formulas (II), (II-1), and (II-2) is an integer of 5; and p' in Formula (II-3) is an integer of 3; R$^1$ and R$^2$ in each of Formulas (II), (II-1), (II-2) and (II-3), which may be the same or different, are each selected from hydrogen, halogen, alkyl (such as C$_{1-6}$ alkyl, further such as methyl), and aryl (such as phenyl); Z in each of Formulas (II), (II-1), (II-2) and (II-3) is independently selected from halogen (such as F, Cl, Br or I) and alkyl (such as C$_{1-6}$alkyl, further such as methyl).

In some embodiments, p in each of Formulas (II), (II-1), and (II-2) is an integer of 6, 7, 8, 9, 10, 11 or 12; and p' in Formula (II-3) is an integer of 4, 5, 6, 7, 8, 9, or 10; R$^1$ and R$^2$ in each of Formulas (II), (II-1), (II-2) and (II-3), which may be the same or different, are each selected from hydrogen, halogen, alkyl (such as C$_{1-6}$ alkyl, further such as methyl), and aryl (such as phenyl); Z in each of Formulas (II), (II-1), (II-2) and (II-3) is independently selected from halogen (such as F, Cl, Br or I) and alkyl (such as C$_{1-6}$alkyl, further such as methyl).

In the third aspect, the at least one compound selected from compounds of Formula (I) and pharmaceutically acceptable salts thereof is selected from compounds of Formula (III) below:

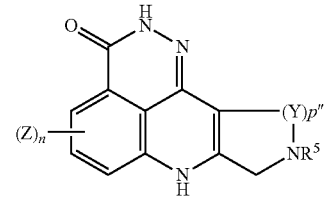

and/or pharmaceutically acceptable salts thereof,
wherein:

Y, at each occurrence, is independently selected from CR$^1$R$^2$—, —R$^3$C=CR$^4$—, —NR$^5$—, —O—, and —S—;

p'' is an integer ranging from 1 to 11, such as from 1 to 4, further such as from 1 to 3, for example, p'' is an integer of 1 or 2;

Z, at each occurrence, is independently selected from hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent $R^9$;

n is an integer ranging from 0 to 3, such as from 0 to 2, for example, n is an integer of 0 or 1;

$R^1$ and $R^2$, which may be the same or different, are each selected from hydrogen, halogen, alkyl, alkenyl, alkynyl, cycloalkyl, aryl, heterocyclyl, heteroaryl, —$NR^6R^7$, —$OR^6$, —$COR^6$, —$CO_2R^6$, —$CONR^6R^7$, —$NR^6CONR^7R^8$, —$NR^6CO_2R^7$, —$NR^6SO_2R^7$, and —$SO_2R^6$, wherein each of the alkyl, alkenyl, alkynyl, cycloalkyl, heteroaryl, aryl, and heterocyclyl is optionally substituted with at least one substituent $R^9$; and when $(Y)_{p''}$ comprises —$CR^1R^2$—$CR^1R^2$—, optionally $R^1$ or $R^2$ substituted on each of the two carbons, together with the two carbons to which they are attached, form a 3- to 8-membered ring optionally substituted with at least one substituent $R^9$, wherein said ring is saturated or partially unsaturated having 0, 1 or 2 heteroatoms independently selected from —$NR^{10}$—, —O—, —S—, —SO— and —$SO_2$—;

$R^3$ and $R^4$, which may be the same or different, are each selected from hydrogen and alkyl, or $R^3$ and $R^4$, together with the atoms to which they are attached, form a 5-, 6-, 7-, or 8-membered ring optionally substituted with at least one substituent $R^9$, wherein said ring is partially or fully unsaturated having 0, 1 or 2 heteroatoms independently selected from —$NR^{10}$—, —O—, —S—, —SO—, and —$SO_2$—;

$R^5$ is independently selected from hydrogen, halogen, alkyl, alkenyl, alkynyl, cycloalkyl, aryl, heterocyclyl, heteroaryl, —$COR^6$, —$CO_2R^6$, —$CONR^6R^7$, $SO_2NR^6R^7$ and —$SO_2R^6$, wherein each of the alkyl, alkenyl, alkynyl, cycloalkyl, heteroaryl, aryl, and heterocyclyl is optionally substituted by at least one substituent $R^9$;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$;

$R^9$, at each occurrence, is independently selected from halogen, haloalkyl, alkyl, alkenyl, cycloalkyl, aryl, heteroaryl, heterocyclyl, alkynyl, oxo, —CN, —OR', —NR'R", —COR', —$CO_2R'$, —CONR'R", —C(=NR')NR"R"', —NR'COR", —NR'CONR'R", —NR'$CO_2R"$, —SR', —SOR', —$SO_2R'$, —NR'$SO_2NR"R'''$, and NR'$SO_2R"$, wherein R', R", and R'" are independently selected from hydrogen, haloalkyl, alkyl, arylalkyl, alkenyl, alkynyl, cycloalkyl, heterocyclyl, aryl, and heteroaryl; and $R^{10}$ is selected from hydrogen, alkyl, cycloalkyl, aryl, heteroaryl and heterocyclyl.

In some embodiments, p" in Formula (III) is an integer of 2. In some embodiments, p" in Formula (III) is an integer of 2 and Y is $CR^1R^2$—, $R^1$ and $R^2$ are defined for Formula (III). In some further embodiments, p" in Formula (III) is an integer of 2 and Y is $CR^1R^2$—, wherein $R^1$ and $R^2$ are hydrogen.

In some embodiments, $R^5$ in Formula (III) is selected from hydrogen, alkyl, —$COR^6$, and —$CO_2R^6$, wherein the alkyl, such as $C_{1-6}$ alkyl, is optionally substituted by at least one substituent $R^9$, such as an aryl group, further such as an phenyl group; and wherein $R^6$ is an alkyl group (such as an $C_{1-6}$alkylgroup) optionally substituted by at least one substituent $R^9$, such as —NR'$CO_2R"$ and —NR'R", wherein R' and R" are independently selected from hydrogen, alkyl (such as $C_{1-6}$alkyl) and arylalkyl (such as aryl-$C_{1-6}$alkyl-, further such as phenyl-$C_{1-6}$alkyl); or $R^6$ is an cycloalkyl group (such as $C_3$, $C_4$, $C_5$, $C_6$, $C_7$, $C_8$ cycloalkyl, further such as $C_3$cycloalkyl) optionally substituted by at least one substituent $R^9$, such as alkyl (such as $C_{1-6}$ alkyl, further such as methyl).

In some embodiments, $R^5$ in Formula (III) is hydrogen.

In some embodiments, n in Formula (III) is an integer of 1, and Z in Formula (III) is selected from the group consisting of halogen, such as F, Cl or Br.

In some embodiments, Formula (I), (II) or (III) may also be presented in the form of their regioisomers (I'), (II') or (III'), respectively,

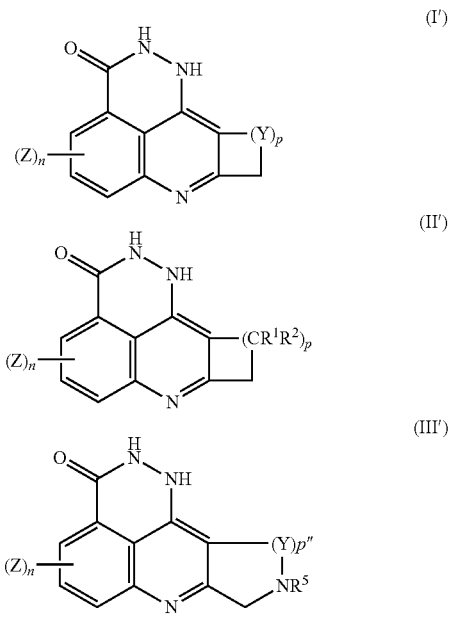

Also provided herein is at least one compound selected from the following compounds and/or pharmaceutically acceptable salts thereof:

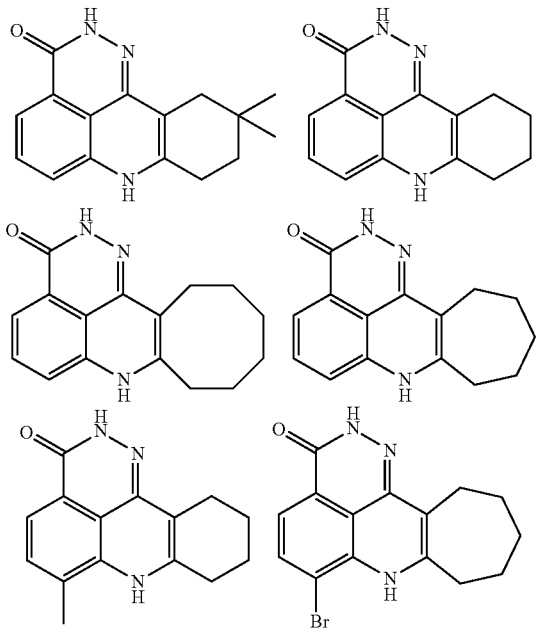

-continued

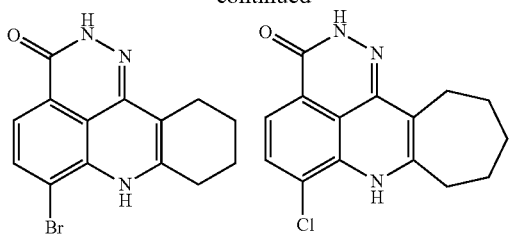

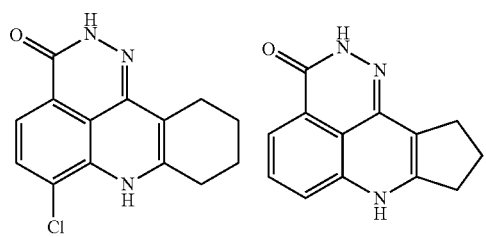

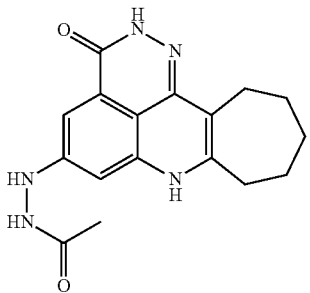

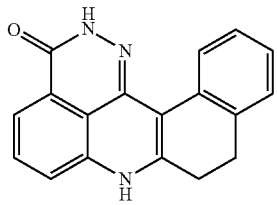

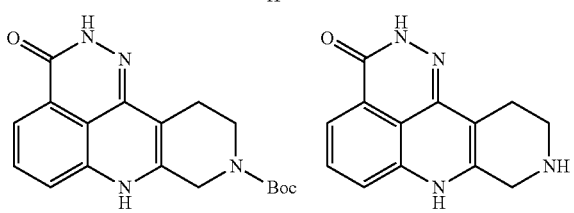

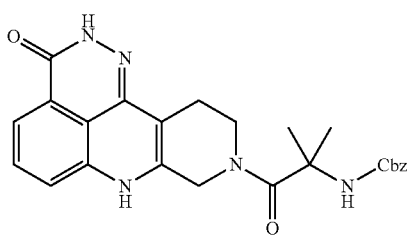

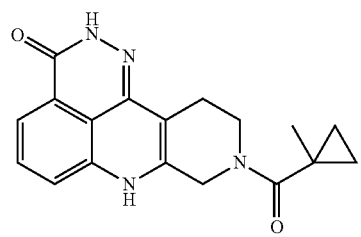

-continued

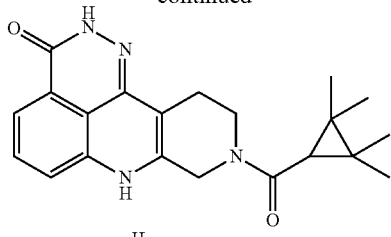

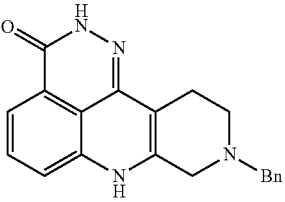

Also provided herein is a method of inhibiting the activity of PARP. The method comprises contacting the PARP with the at least one compound and/or at least one pharmaceutically acceptable salt thereof described herein in an amount effective to inhibit the activity of the PARP.

Also provided herein is a method of treating at least one disease responsive to inhibition of PARP comprising administering to a subject, such as a mammal or human, in recognized need of such treating for the at least one disease an amount of at least one compound and/or at least one pharmaceutically acceptable salt thereof described herein.

The at least one disease can be selected from, for example, ovarian cancer, carcinomas of the breast, colon cancer, leukemia, glioblastomas, lymphomas, melanomas, cervial carcinomas and other cytotoxic cancers.

The at least one compound and/or at least one pharmaceutically acceptable salt thereof disclosed herein may be employed alone or in combination with radiation and chemotherapy by, for example, increasing apoptosis of cancer cells, limiting tumor growth, decreasing metastasis, and prolonging the survival of tumor-bearing mammals.

In some embodiments, the at least one compound and/or at least one pharmaceutically acceptable salt thereof disclosed herein can be used in combination with at least one additional therapeutic agent, such as at least one additional chemotherapeutic agent.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-α and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gamma1I and calicheamicin omega1I (Angew Chem. Intl. Ed. Engl. (1994) 33: 183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolinodoxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle Formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, such as those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the at least one compound and/or at least one pharmaceutically acceptable salt thereof disclosed herein may, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Also provided herein is a composition comprising at least one compound and/or at least one pharmaceutically acceptable salt thereof disclosed herein, and at least one pharmaceutically acceptable carrier.

The composition comprising at least one compound and/or at least one pharmaceutically acceptable salt disclosed herein can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The at least one compound and/or at least one pharmaceutically acceptable salt thereof disclosed herein can be administered orally in solid dosage forms, such as capsules, tablets, troches, dragées, granules and powders, or in liquid dosage forms, such as elixirs, syrups, emulsions, dispersions, and suspensions. The at least one compound and/or at least one pharmaceutically acceptable salt thereof disclosed herein can also be administered parenterally, in sterile liquid dosage forms, such as dispersions, suspensions or solutions. Other dosages forms that can also be used to administer the at least one compound and/or at least one pharmaceutically acceptable salt thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one phareeutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

Suitable in vitro assays can be used to preliminarily evaluate the efficacy of the at least one compound and/or at least one pharmaceutically acceptable salt thereof disclosed herein, in inhibiting the activity of PARP. The at least one compound and/or at least one pharmaceutically acceptable salt thereof disclosed herein can further be examined for efficacy in treating cancer by in vivo assays. For example, the at least one compound and/or the at least one pharmaceutically acceptable sals thereof disclosed herein can be administered to an animal (e.g., a mouse model) having cancer and its therapeutic effects can be accessed. Positve results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the at least one compound and/or at least one pharmaceutically acceptable salt thereof disclosed herein may be conveniently delivered in the form of an aerosol spray presentation from pressurized packs or nebulisers. The at least one compound and/or at least one pharmaceutically acceptable salt thereof disclosed herein may also be delivered as powders, which may be Formulated and the powder composition may be inhaled with the aid of an insufflation powder inhaler device. One exemplary delivery system for inhalation can be a metered dose inhalation (MDI) aerosol, which may be Formulated as a suspension or solution of at least one compound and/or at least one pharmaceutically acceptable salt thereof disclosed herein in at least one suitable propellant, selected, for example, from fluorocarbons and hydrocarbons.

For ocular administration, an ophthalmic preparation may be Formulated with an appropriate weight percentage of a solution or suspension of the at least one compound and/or at least one pharmaceutically acceptable salt thereof disclosed herein in an appropriate ophthalmic vehicle, such that the at least one compound and/or at least one pharmaceutically acceptable salt thereof disclosed herein is maintained in contact with the ocular surface for a sufficient time period to allow the compound to penetrate the corneal and internal regions of the eye.

Useful pharmaceutical dosage-forms for administration of the at least one compound and/or at least one pharmaceutically acceptable salt thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain desired results.

In some embodiments, a large number of unit capsules can be prepared by filling standard two-piece hard gelatin capsules each with, for example, 100 milligrams of the at least one compound and/or at least one pharmaceutically acceptable salt thereof disclosed herein in powder, 150 milligrams of lactose, 50 milligrams of cellulose, and 6 milligrams magnesium stearate.

In some embodiments, a mixture of the at least one compound and/or at least one pharmaceutically acceptable salt thereof disclosed herein in a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the at least one compound and/or at least one pharmaceutically acceptable salt thereof disclosed herein, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least one pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided at least one compound and/or at least one pharmaceutically acceptable salt thereof disclosed herein, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the at least one compound and/or at least one pharmaceutically acceptable salt thereof disclosed herein are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The at least one compound and/or at least one pharmaceutically acceptable salt thereof disclosed herein can be administered as the sole active ingredient or in combination with at least one second active ingredient, selected, for example, from other active ingredients known to be useful for treating cancers in a patient.

General Synthetic Shemes

The compounds disclosed herein, and/or the pharmaceutically acceptable salts thereof, can be synthesized from commercially available starting materials taken together with the disclosure herein. The following schemes illustrate methods for preparation of some of the compounds disclosed herein.

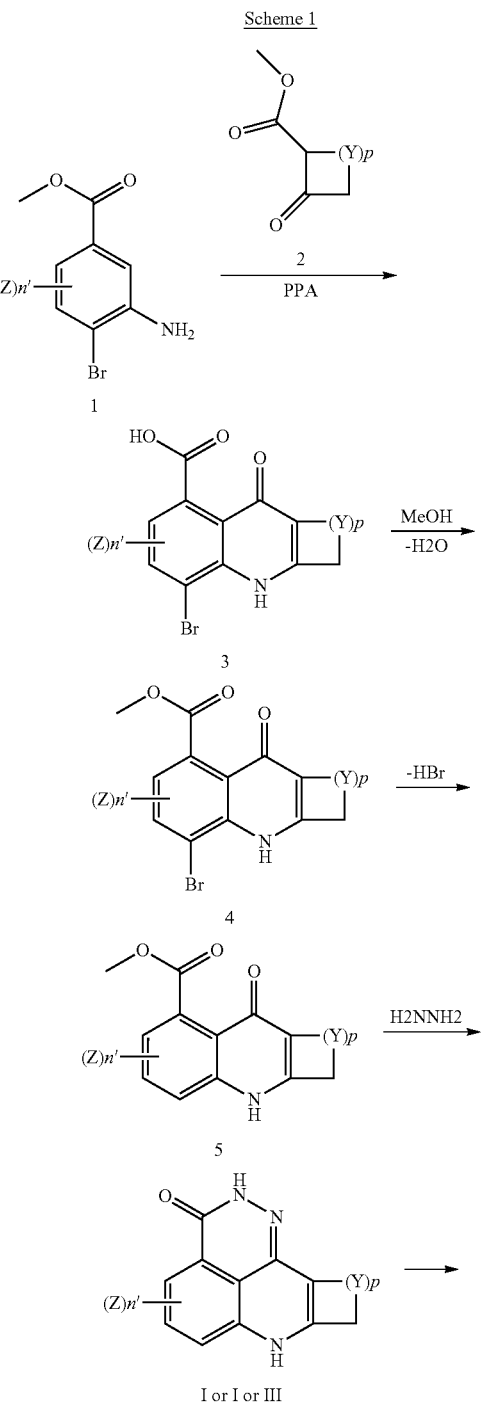

-continued

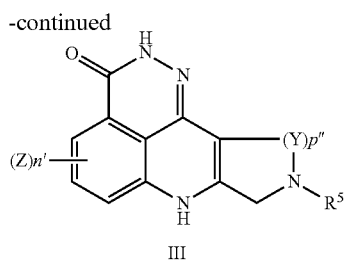

Wherein Z, Y, p are defined as for Formula (I);
n' is an integer of 0, 1, or 2;
$R^5$ and p" are defined as for Formula (III)

In this scheme, an alkyl 3-amino-4-bromo-benzoate of Formula 1 is reacted with a cyclic ketoester of Formula 2 to provide a bromoquinolinone carboxylic acid of Formula 3. The following esterification with alcohol and debromination under hydrogenolysis condition using a catalyst, such as palladium, gives an alkyl 4-oxo-1,4-dihydroquinoline-5-carboxylate of Formula 5 which is subsequently cyclized with hydrazine to provide the pyridinophthalazinone derivative of Formula (I). When the —(Y)p-moiety in Formula (I) is —(Y)p"-NH—, NH undergoes a typical alkylation with alkyl halide and a base, reductive alkylation with ketone/aldehyde and a reducing agent, acylation with acyl chloride or acid and a coupling agent, with help of a coupling reagent, or sulfonylation with sulfonyl chloride and a base, to provide final compound of Formula (III).

The first step of this scheme is conducted in PPA with a solvent such as dioxane or ethanol. The resulting bromoquinolinone carboxylic acid of Formula 3 is purified on a flash column or directly precipitated out of the reaction solution.

The second step of this scheme can be conducted using a mixture of trimethylsilyl chloride/methanol or thionyl chloride/methanol at room temperature or under refluxing. The resulting ester 4 can be precipitated out of the reaction mixture or purified on chromatography.

The third step of this scheme is performed under hydrogenolysis condition with a catalyst such as palladium on carbon. This reaction is completed in 5-12 hrs at room temperature in a solvent such as methanol, ethanol and under a hydrogen balloon. The resulting de-bromo ester 5 is normally used for further reaction without purification or is purified on chromatography for analytical purpose.

The fourth step of the synthesis of the novel compounds of Formula (I) or (II) is a cyclization reaction of a compound of Formula 5 to provide the pyridophthalazinone derivatives of Formula (I) as shown in Scheme 1. This cyclization reaction can be typically conducted using 1-2 equivalents of hydrous hydrazine and the appropriate alcohol as solvent. The cyclization reaction can be typically conducted at a temperature ranging from 50° C. to the refluxing temperature of the solvent and it can be completed, for instance, in 1 to 12 hrs. The compound of Formula (I) or (II) can be precipitated out of the reaction mixture or separated on chromatography. The recrystallization can be carried out in a solvent or a mixture of solvents such as dioxane or methanol/dichloromethane. The compound of Formula (III) is prepared by derivatizing the NH position of Formula (I).

For example, the direct coupling of the compound of Formula (I) with an acid can be accomplished under appropriate reagents such as EDC/DIEA in a solvent such as dichloromethane.

In the above scheme, the intermediate 3, 4, 5 may also be presented in the form of their regioisomers 3', 4', and 5', respectively,

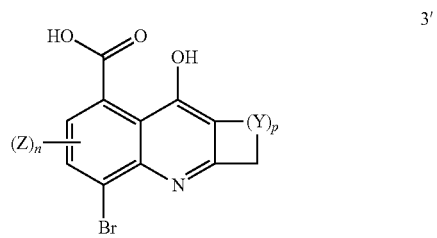

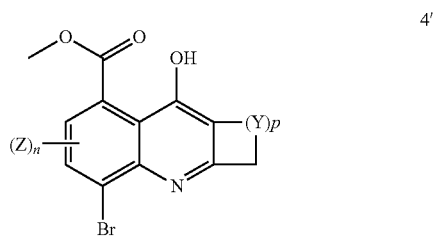

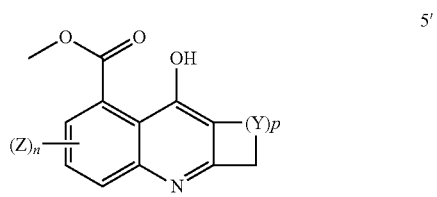

In the above scheme, the final compounds (I), (II) and (III) may also be presented in the form of regioisomers (I'), (II') and (III'), respectively,

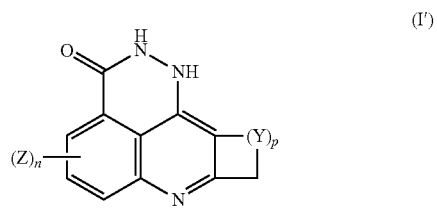

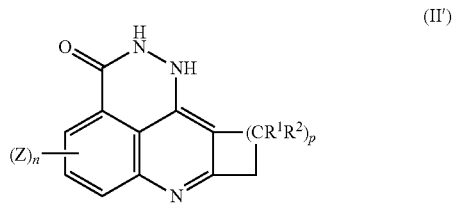

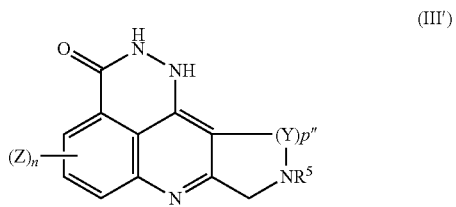

In certain examples, an alternative synthesis of the final compound (I) is described in the Scheme 2.

Scheme 2

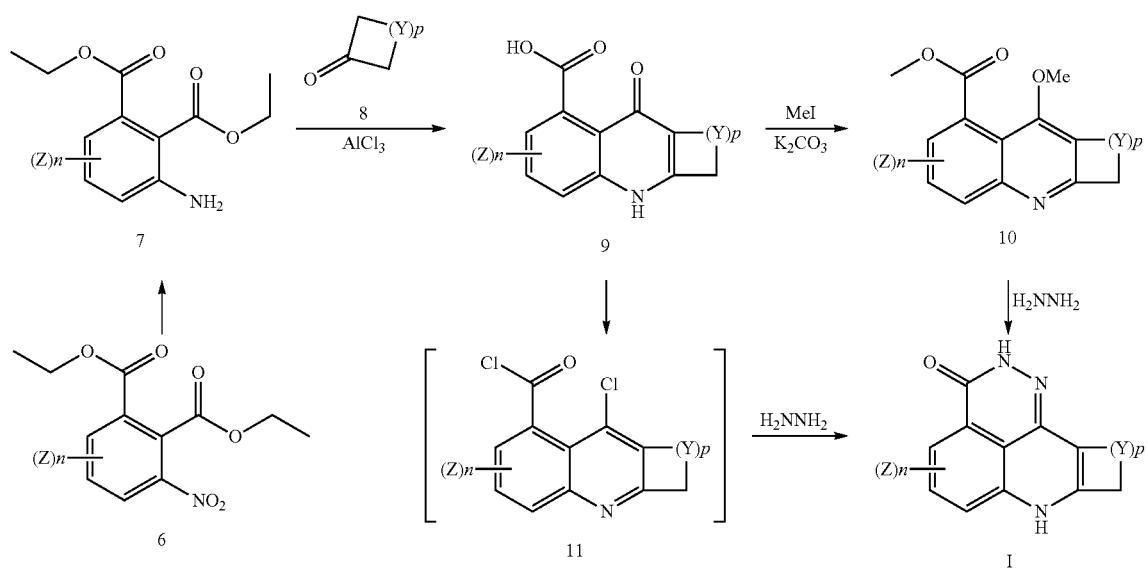

In Scheme 2, diethyl 3-nitrophthalate of Formula 6 is converted into diethyl 3-aminophthalate of Formula 7 under hydrogenation condition. The following condensation with a cyclic ketone 8 under Lewis acid condition provides aquinolinone carboxylic acid of Formula 9. The double methylation of quinolinone carboxylic acid 9 with methyl iodide and potassium carbonate gives an ester of Formula 10 which is subsequently cyclized with hydrazine to provide the pyridinophthalazinone derivative of Formula (I). Alternatively, quinolinone carboxylic acid 9 is treated with trichlorophosphoxide and then the resulting intermediate 11 is immediately treated with hydrazine to give the final compound of Formula (I).

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1$H NMR spectra were recorded on a Varian instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; (CD3) 2CO: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by Chemdraw version 12.0.

In the following examples, the abbreviations below are used:
AcOH Acetic acid
Aq Aqueous
Brine Saturated aqueous sodium chloride solution
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
G grams
h or hr hour
HATU 2-(1H-7-Azabenzotriazol-1-yl)-1,1,3,3-tetramethyl uronium hexafluorophosphate Methanaminium
HCl Hydrochloric acid
HPLC High-performance liquid chromatography
IPA 2-propanol
i-PrOH Isopropyl alcohol
Mg milligrams
mL milliliters
Mmol millimole
MeCN Acetonitrile
MeOH Methanol
Min minutes
ms or MS Mass pectrum Na₂SO₄ Sodium sulfate
PPA Polyphosphoric acid
Rt Retention time
Rt or rt Room temperature
TFA Trifluoroacetic acid
THF tetrahydrofuran
TLC thin layer chromatography
TMSCl Trimethylsilyl chloride
μL Microliters Example 1

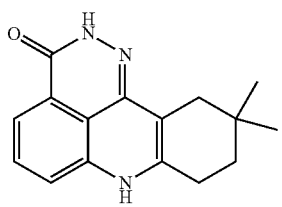 [SMILES: CC1(C)CCC2=C(C1)c1n[nH]c(=O)c3cccc(c13)N2]

Step 1: Methyl 2-hydroxy-5,5-dimethylcyclohex-1-enecarboxylate

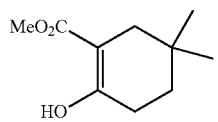

To a solution of dimethyl carbonate (31.5 g, 350 mmol) in dry THF (600 mL) was added sodium hydride (14.4 g, 360 mmol) by portion at 0° C. The resulting mixture was stirred at 0° C. for 30 min and then was added a solution of 4,4-dimethylcyclohexanone (15 g, 119 mmol) in THF (150 mL) dropwise over 30 min. The resultant mixture was heated at 60° C.-80° C. for 3 h before cooled to room temperature. The reaction mixture was poured into saturated NaHCO₃ solution and extracted with a mixture of 33% ethyl acetate in petroleum ether. The organic layer was washed with water, brine, dried over Na₂SO₄ and concentrated to give 26.5 g crude of methyl 2-hydroxy-5,5-dimethylcyclohex-1-enecarboxylate, which was used in next step without further purification. ¹H NMR (DMSO-d6) δ 12.09 (s, 1H), 3.71 (s, 3H), 2.25-2.26 (m, 2H), 1.99 (s, 2H), 1.40-1.41 (m, 2H), 0.92 (s, 1H).

Step 2: Methyl 4-bromo-7,7-dimethyl-9-oxo-5,6,7,8,9,10-hexahydroacridine-1-carboxylate

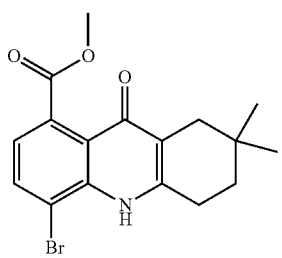 [SMILES: COC(=O)c1ccc(Br)c2[nH]c3c(c(=O)c12)CC(C)(C)CC3]

A mixture of methyl 2-hydroxy-5,5-dimethylcyclohex-1-enecarboxylate (26 g, 0.141 mol), methyl 3-amino-4-bromobenzoate (25 g, 0.109 mol), polyphosphoric acid (220 g) and dioxane (220 mL) was heated at 130° C. for 5 hours. After cooling, the mixture was diluted with water. The resulting precipitate was collected by filtration and dried. The solid was suspended in methanol (400 mL), and TMSCl (90 mL) was added. The mixture was stirred at reflux for 5 hours, concentrated and treated with water (80 mL), extracted with ethyl acetate (250 mL). The organic layer was separated, concentrated and recrystallized with methanol to afford desired compound (10.6 g, 27%). ¹H NMR (DMSO-d6) δ 10.32 (s, 1H), 7.98 (d, 1H, J=7.2 Hz), 7.10 (d, 1H, J=7.2 Hz), 3.80 (s, 3H), 2.90 (t, 2H, J=6.6 Hz), 2.22 (s, 2H), 1.56 (t, 2H, J=6.6 Hz), and 0.97 (s, 6H). MS (ESI) m/e [M+1]⁺364.

Step 3: Methyl 7,7-dimethyl-9-oxo-5,6,7,8,9,10-hexahydroacridine-1-carboxylate

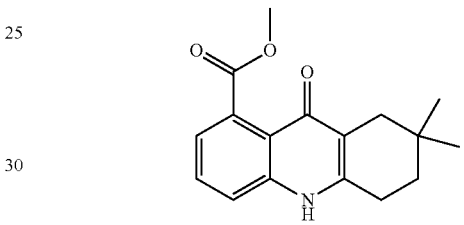

A mixture of methyl 4-bromo-7,7-dimethyl-9-oxo-5,6,7,8,9,10-hexahydro-acridine-1-carboxylate (4.0 g, 11 mmol), ethyl acetate (300 mL), Pd/C (5% Pd on carbon, 50% water, 4.0 g) was stirred at room temperature under an atmosphere of hydrogen for 6 hours. Methanol (100 mL) and Pd/C (5% Pd on carbon, 50% water, 8.0 g) was added to the mixture and stirred for another 1 hour. The mixture was filtered through celite and the filtrate was concentrated to give the desired product (3.3 g, crude) which was used to next step without further purification. 1H NMR (DMSO-d6) δ 11.70-11.72 (m, 1H), 7.60-7.63 (m, 2H), 7.13-7.14 (m, 1H), 3.79 (s, 3H), 2.76-2.77 (m, 2H), 2.23 (s, 2H), 1.55-1.57 (m, 2H), and 0.97 (s, 6H). MS (ESI) m/e [M+1]⁺286.

Step 4: 10,10-Dimethyl-8,9,10,11-tetrahydro-2H-pyridazino[5,4,3-kl]acridin-3(7H)-one

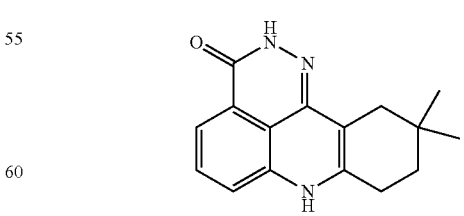

A solution of 7,7-dimethyl-9-oxo-5,6,7,8,9,10-hexahydroacridine-1-carboxylate (3.3 g, 11.6 mmol) and hydrazine hydrate (15 mL) in DMA (22 mL) was heated at 110° C. for 1.5 h, acetic acid (30 mL) was added and the mixture was stirred at 130° C. for another 4 hours. The reaction mixture was cooled to room temperature, and aqueous NaHCO₃ (80 ml) was added to the mixture, filtered. And the filtered cake was washed with water (50 mL) and methanol (30 mL) alternatively multiple times. The solvent was removed in vacuo to give 10,10-Dimethyl-8,9,10,11-tetrahydro-2H-pyridazino[5,4,3-kl]acridin-3(7H)-one as a yellow solid (1.50 g, 49%). ¹H NMR (DMSO-d6) δ 11.71 (s, 1H), 10.36 (s, 1H), 7.59-7.63 (m, 1H), 7.42-7.44 (m, 1H), 7.25-7.27 (m, 1H), 2.49-2.52 (m, 2H), 2.10 (s, 2H), 1.55 (m, 2H), and 1.00 (s, 6H). MS (ESI) m/e [M+1]⁺268.

Example 2

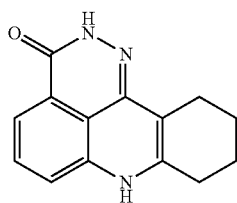 [SMILES: O=c1[nH]nc2c3c(cccc13)NC1=C2CCCC1]

8,9,10,11-Tetrahydro-2H-pyridazino[5,4,3-kl]acridin-3 (7H)-one

A mixture of methyl 2-oxocyclohexanecarboxylate (1.70 g, 10 mmol), 3-amino-4-bromobenzoic acid (2.16 g, 10 mmol), polyphosphoric acid (15 g) and dioxane (12 mL) was heated at 130° C. for 5 hours. After cooling to room temperature, NaOAc.3H₂O (27 g) was added and the pH≈3. Then the mixture was diluted with water and the resulting precipitate was collected by filtration and dried. The solid was suspended in methanol (80 mL) and SOCl₂ (16 mL) was added at 0-15° C., the mixture was stirred at reflux for 5 hours. After cooling to room temperature, the mixture was concentrated and treated with water (100 mL), extracted with ethyl acetate (3×100 mL), the organic layer was separated, and concentrated to afford the crude product. Then the mixture was purified by chromatography column on silica gel (eluted with CH₂Cl₂/MeOH) to afford methyl 4-bromo-9-oxo-5,6,7,8,9,10-hexahydroacridine-1-carboxylatet (2.20 g). MS (ESI) m/e [M+1]⁺336.

A mixture of methyl 4-bromo-9-oxo-5,6,7,8,9,10-hexahydroacridine-1-carboxylate (0.19 g, 0.56 mmol), MeOH (20 mL), and Pd/C (5% Pd on carbon, 50% water, 0.05 g) were stirred at room temperature under an atmosphere of hydrogen for 6 hours. The mixture was filtered through celite and the filtrate was concentrated to give crude methyl 9-oxo-5,6,7,8,9,10-hexahydroacridine-1-carboxylate (0.22 g), which was used to next step without further purification.

To the solution of the crude methyl 9-oxo-5,6,7,8,9,10-hexahydroacridine-1-carboxylate in DMA (4 mL) was added hydrazine hydrate (4 mL) at room temperature, and the mixture was heated at 130° C. for 4.0 h. The reaction mixture was cooled to room temperature and stirred for another 12 hours. Then the mixture was filtered and recrystallized from MeOH (twice) to give the product (20 m g, 15%) as a yellow solid.

¹H NMR (CD₃OD-d4) δ 7.66 (t, 1H, J=7.8 Hz), 7.59 (dd, 1H, J=7.8, 1.2 Hz), 7.29 (dd, 1H, J=7.8, 1.2 Hz), 2.54-2.56 (m, 2H), 2.40-2.42 (m, 2H), 1.84-1.89 (m, 4H). MS (ESI) m/e [M+1]⁺240.0.

Example 3

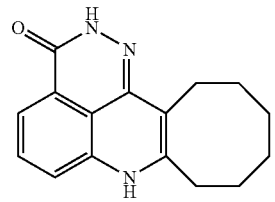 [SMILES: O=c1[nH]nc2c3c(cccc13)NC1=C2CCCCCC1]

Step 1: Methyl 2-oxocyclooctanecarboxylate

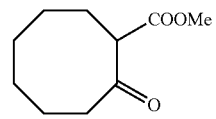 [SMILES: COC(=O)C1CCCCCCC1=O]

To a solution of dimethyl carbonate (30 mL, 0.36 mol) in dry THF (600 mL) was added sodium hydride (15 g, 0.36 mol) by portion at 5-10° C. The resulting mixture was stirred at this temperature for 30 min and then was added a solution of cyclooctanone (15.0 g, 0.12 mol) in THF (100 mL) dropwise over 30 min. The resultant mixture was stirred at refluxed for 4 h before cooling to room temperature. The reaction mixture was poured into saturated NaHCO₃ solution (100 mL) and ice (500 g), and then the mixture was extracted with PE/EA (4:1, 400 mL×2). The organic layer was washed with brine (400 mL), dried over Na₂SO₄ and concentrated to give crude product. Then the target product (19.3 g, 88%) was purified by distilling at 60° C. in vacuum.

Step 2: Methyl 3-amino-4-bromobenzoate

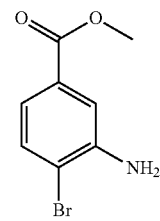

4-Bromo-3-nitrobenzoic acid (42 g; 170 mmol.) is dissolved in MeOH (100 ml). Con.H₂SO₄ (10 mL) is added dropwise at 0° C. The solution is stirred at reflux for 4.0 h before cooled to room temperature. Then cooled water (100 mL) was added, and the precipitate was filtrated, washed with water to afford a white solid (48 g), which was used to the next step without further purification.

Then the crude product (48 g) and Na₂S₂O4 (88 g) were dissolved in MeOH/water (565 mL/170 mL), and the mixture was stirred at reflux until the starting material was consumed (about 4 h). After cooling to room temperature, the solvent was evaporated and the crude reaction mixture was treated with aqueous of Na$_2$CO$_3$ (10%, 200 mL) and EtOAc (3×100 mL), and the two layers were separated in a separation funnel. The organic layer was washed with water (100 mL), brine (100 mL), dried, evaporated to get the crude product (13 g) which was used without further purified. $^1$H NMR (DMSO-d$_6$) δ 7.48 (d, 1H, J=8.4 Hz), 7.42 (d, 1H, J=2.4 Hz), 7.03 (dd, 1H, J=8.4, 2.4 Hz), and 3.82 (s, 3H).

Step 3: Methyl 4-bromo-12-oxo-5,6,7,8,9,10,11,12-octahydrocycloocta[b]quinoline-1-carboxylate

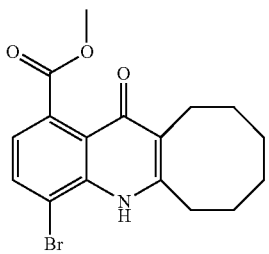 [SMILES: COC(=O)c1ccc(Br)c2[nH]c3c(c(=O)c12)CCCCCC3]

A mixture of methyl 2-oxocyclooctanecarboxylate (32.0 g, 174 mmol), methyl 3-amino-4-bromobenzoate (20.0 g, 87 mmol) and ethanol (120 mL) was heated to reflux, at an oil bath of 130° C., acetic acid (1.5 mL) was added and the mixture was reflux for 1.5 hours. Hot PPA (200 g, 120° C.) was added to the reaction mixture carefully. The reaction mixture was heated at an oil bath of 130° C. for 3 hours. After cooling for a while, ice (200 g), ethyl acetate (60 mL) and petroleum ether (60 mL) were added to the reaction mixture, the mixture was concentrated until 200 mL solvent was removed. Then water (600 mL) and ethyl acetate (60 mL) were added, the resulting mixture was stayed at room temperature overnight. A light brown solid was slowly formed. The mixture was filtered and the filtered cake was dried to give a light brown solid, which was placed into methanol (90 mL). SOCl$_2$ (30 mL) was added dropwise with cooling with an ice-bath. The resulting mixture was heated to reflux for 4 hours, concentrated and treated with saturated NaHCO$_3$ solution (60 mL) and ethyl acetate (30 mL), filtered and the filtered cake was dried to give desired product (6.6 g) as a pale white solid (21%). $^1$H NMR (DMSO-d$_6$) δ10.25 (s, 1H), 7.96-7.98 (d, 1H, J=7.6 Hz), 7.09-7.11 (d, 1H, J=7.6 Hz), 3.02-3.06 (m, 2H), 2.63-2.66 (m, 2H), 1.75-1.77 (m, 2H), 1.53-1.55 (m, 2H), and 1.36-1.39 (m, 4H). MS (ESI) m/e [M+1]$^+$ 364/366.

Step 4: 8,9,10,11,12,13-Hexahydro-2H-cycloocta[5,6]pyrido[4,3,2-de]phthalazin-3(7H)-one

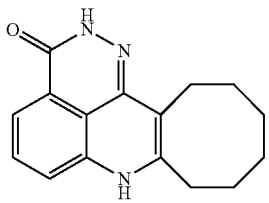 [SMILES: O=c1[nH]nc2c3c(cccc13)NC1=C2CCCCCC1]

A mixture of methyl 4-bromo-12-oxo-5,6,7,8,9,10,11,12-octahydrocycloocta[b]quinoline-1-carboxylate (6.0 g, 15.9 mmol), MeOH (120 mL), ethyl acetate (180 mL), and Pd/C (5% Pd on carbon, 50% water, 3.0 g) were stirred at room temperature under an atmosphere of hydrogen for 4 hours. The mixture was filtered through celite and the filtrate was concentrated to give a brown solid (6.3 g) which was used to next step without further purification. The solid was dissolved in DMA (72 mL), hydrazine hydrate (48 mL) was added and heated at 110° C. for 3 h, acetic acid (96 mL) was added and the mixture was stirred at an oil bath of 130° C. for another 6.5 hours. The reaction mixture was cooled to room temperature, carefully poured into NaHCO$_3$ aqueous (400 ml), filtered and the filtered cake was ultrasonicated in methanol (60 mL) for 40 minutes, filtered. The filtered cake was repeated with sonication and filtration for another 6 times. The filtered cake was dried to give the desired product (2.9 g, 68%) as a yellow solid. $^1$H NMR (DMSO-d$_6$) δ 11.66 (s, 1H), 10.33 (s, 1H), 7.58 (t, 1H, J=7.8 Hz), 7.41 (d, 1H, J=7.8 Hz), 7.23 (d, 1H, J=7.8 Hz), 2.59-2.65 (m, 4H), 1.70-1.72 (m, 2H), 1.56-1.58 (m, 2H), 1.44-1.47 (m, 4H). MS (ESI) m/e [M+1]$^+$268.0.

Example 4

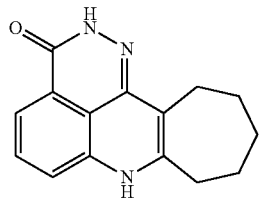 [SMILES: O=c1[nH]nc2c3c(cccc13)NC1=C2CCCCC1]

7,8,9,10,11,12-Hexahydrocyclohepta[5,6]pyrido[4,3,2-de]phthalazin-3(2H)-one

Example 4 was prepared from methyl 3-amino-4-bromobenzoate and methyl 2-oxocycloheptanecarboxylate according to the same procedures described as those in Example 3. $^1$H NMR (CD$_3$OD-d4) δ 7.58 (dd, 1H, J=8.0, 7.6 Hz), 751 (d, 1H, J=7.6 Hz), 7.22 (d, 1H, J=8.0 Hz), 2.63-2.75 (m, 4H), 1.82-1.87 (m, 2H), 1.65-1.70 (m, 2H), 1.51-1.57 (m, 2H). MS (ESI) m/e [M+1]$^{30}$ 254.0.

Example 5

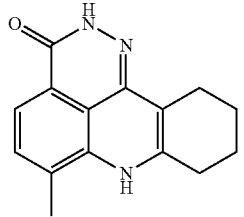 [SMILES: Cc1ccc2c(=O)[nH]nc3c2c1NC1=C3CCCC1]

Step 1: Methyl 4-methyl-9-oxo-5,6,7,8,9,10-hexahydroacridine-1-carboxylate

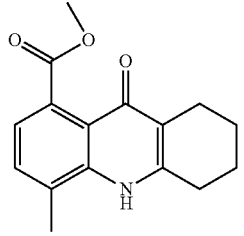 [SMILES: COC(=O)c1ccc(C)c2[nH]c3c(c(=O)c12)CCCC3]

A mixture of methyl 2-oxocyclohexanecarboxylate (1.0 g, 6.4 mmol), methyl 3-amino-4-methylbenzoate (1.06 g, 6.4 mmol), polyphosphoric acid (4 mL) and dioxane (6 mL) was heated at 130° C. for 2 hours. After cooling to room temperature, the mixture was diluted with water (100 mL) and the resulting precipitate was collected by filtration and dried. The solid was suspended in methanol (100 mL) and SOCl$_2$ (10 mL) was added. The mixture was stirred at reflux for 5 hours, concentrated and treated with water (80 mL), extracted with ethyl acetate (3×80 mL). The organic layer was separated, concentrated to give the crude product. Then the mixture was purified by chromatography column on silica gel (eluted with CH$_2$Cl$_2$/MeOH) to afford crude product, and the final product (0.55 g) was obtained from recrystallization using MeOH as solvent. $^1$H NMR (DMSO-d$_6$) δ 10.3 (s, 1H), 7.41 (d, 1H, J=7.8 Hz), 6.99 (d, 1H, J=7.8 Hz), 3.73 (s, 3H), 2.78-2.81 (m, 2H), 2.50 (s, 3H), 2.35-2.37 (m, 2H), and 1.64-1.73 (m, 4H). MS (ESI) m/e [M+1]$^+$272.0.

Step 2: 6-Methyl-8,9,10,11-tetrahydro-2H-pyridazino[5,4,3-kl]acridin-3(7H)-one

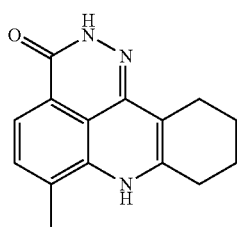 [SMILES: Cc1ccc2c(=O)[nH]nc3c2c1NC1=C3CCCC1]

A solution of methyl 9-hydroxy-7,7-dimethyl-5,6,7,8-tetrahydroacridine-1-carboxylate (0.18 g, 0.63 mmol) and hydrazine hydrate (2.5 mL) in DMA (4 mL) was heated at 130° C. for 4 hours. The reaction mixture was cooled to room temperature, the resulting precipitate was collected by filtration, washed with MeOH (cold, 5 mL) and water (30 mL). Then the precipitate was recrystalized with MeOH to afford a yellow solid (95 mg). $^1$H NMR (DMSO-d$_6$) δ 11.6 (s, 1H), 9.05 (s, 1H), 7.46 (d, 1H, J=7.8 Hz), 7.38 (d, 1H, J=7.8 Hz), 2.52-2.54 (m, 2H), 2.34 (s, 3H), 2.24-2.26 (m, 2H), 1.68-1.72 (m 4H). MS (ESI) m/e [M+1]$^+$254.0.

Example 6

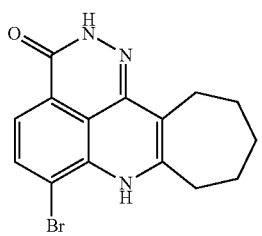 [SMILES: O=c1[nH]nc2c3c(c(Br)ccc13)NC1=C2CCCCC1]

6-Bromo-7,8,9,10,11,12-hexahydrocyclohepta[5,6]pyrido[4,3,2-de]phthalazin-3(2H)-one Example 6 was prepared from methyl 3-amino-4-bromobenzoate and methyl 2-oxocycloheptanecarboxylate according to the same procedures described as those in Example 5. $^1$H NMR (DMSO-d$_6$) δ 11.8 (s, 1H), 9.02 (s, 1H), 7.86 (d, 1H, J=7.8 Hz), 7.46 (d, 1H, J=7.8 Hz), 2.66-2.82 (m, 4H), 1.73-1.75 (m, 2H), 1.55-1.57 (m, 2H), and 1.44-1.45 (m, 2H). MS (ESI) m/e [M+1]$^+$332.0.

Example 7

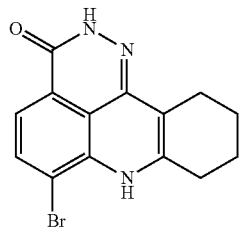 [SMILES: O=c1[nH]nc2c3c(c(Br)ccc13)NC1=C2CCCC1]

6-Bromo-8,9,10,11-tetrahydro-2H-pyridazino[5,4,3-kl]acridin-3(7H)-one

Example 7 was prepared from methyl 3-amino-4-bromobenzoate and methyl 2-oxocyclohexanecarboxylate according to the same procedures described as those in Example 5. $^1$H NMR (DMSO-d$_6$) δ 11.9 (s, 1H), 9.19 (s, 1H), 7.93 (d, 1H, J=8.4 Hz), 7.43 (d, 1H, J=8.4 Hz), 2.61-2.63 (m, 2H), 2.31-2.32 (m, 2H), and 1.72-1.76 (m, 4H). MS (ESI) m/e [M+1]$^+$320.0.

Example 8

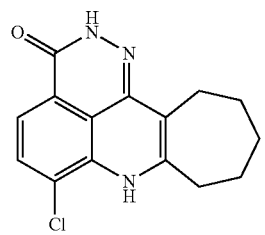 [SMILES: O=c1[nH]nc2c3c(c(Cl)ccc13)NC1=C2CCCCC1]

6-Chloro-7,8,9,10,11,12-hexahydrocyclohepta[5,6]pyrido[4,3,2-de]phthalazin-3(2H)-one Example 8 was prepared from methyl 3-amino-4-chlorobenzoate and methyl 2-oxocycloheptanecarboxylate according to the same procedures described as those in Example 5. $^1$H NMR (DMSO-d$_6$) δ 11.9 (s, 1H), 9.40 (s, 1H), 7.75 (d, 1H, J=7.8 Hz), 7.46 (d, 1H, J=7.8 Hz), 2.83-2.85 (m, 2H), 2.69-2.71 (m, 2H), 1.78-1.79 (m, 2H), 1.59-1.60 (m, 2H), and 1.47-1.48 (m, 2H). MS (ESI) m/e [M+1]$^+$288.0.

Example 9

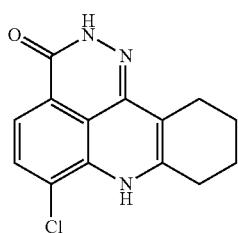 [SMILES: O=c1[nH]nc2c3c(c(Cl)ccc13)NC1=C2CCCC1]

6-Chloro-8,9,10,11-tetrahydro-2H-pyridazino[5,4,3-kl]acridin-3(7H)-one

Example 9 was prepared from methyl 3-amino-4-chlorobenzoate and methyl 2-oxocyclohexanecarboxylate according to the same procedures described as those in Example 5. $^1$H NMR (DMSO-d$_6$) δ 7.71 (d, 1H, J=8.4 Hz), 7.56 (d, 1H, J=7.8 Hz), 2.58-2.60 (m, 2H), 2.36-2.40 (m, 2H), 1.78-1.84 (m, 4H). MS (ESI) m/e [M+1]$^+$274.0.

Example 10

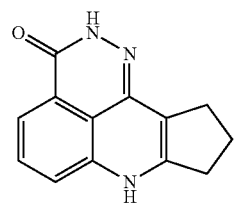 [SMILES: O=c1[nH]nc2c3c(cccc13)NC1=C2CCC1]

Step 1: 9-Oxo-2,3,4,9-tetrahydro-1H-cyclopenta[b]quinoline-8-carboxylic acid

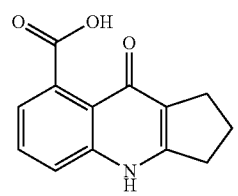 [SMILES: O=C(O)c1cccc2[nH]c3c(c(=O)c12)CCC3]

To the solution of methyl 3-aminobenzoate (302 mg, 2.0 mmol) and methyl 2-oxocyclopentanecarboxylate (284 mg, 2.0 mmol) in MeOH (10 mL) were added MgSO4 (240 mg) and concentrated HCl (2 drops), the mixture was heated to 60° C. for 4.0 h. After cooling to room temperature, the solvent was evaporated in vacuum. The mixture was filtered and washed with EtOAc (15 mL), the solvent was evaporated and used for the next step without further purification. The crude mixture was dissolved in PPA (4.0 mL), and was stirred in 130° C. for 3 h. After cooling to the room temperature, water (20 mL) was added, and the mixture was extracted with EtOAc (50 mL×3). The organic layers were combined, dried over Na$_2$SO$_4$, and concentrated to afford the mixture, which was purified on Pre-HPLC to afford 9-oxo-2,3,4,9-tetrahydro-1H-cyclopenta[b]quinoline-8-carboxylic acid as a white solid. MS (ESI) m/e [M+1]$^+$230.0

Step 2: 7,8,9,10-Tetrahydrocyclopenta[5,6]pyrido[4,3,2-de]phthalazin-3(2H)-one

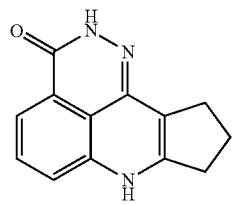

9-Oxo-2,3,4,9-tetrahydro-1H-cyclopenta[b]quinoline-8-carboxylic acid (46 mg) was dissolved in the MeOH (2.0 mL), and SOCl$_2$ (0.3 mL) was added, the mixture was heated to 70° C. for 4.0 h. After cooling to room temperature, the solvent was evaporated and the crude product was dissolved in DMA (2.0 mL), then NH$_2$NH$_2$.H$_2$O (2.0 mL) and CH$_3$COOH (1.0 mL) were added. The mixture was subsequently stirred at 130° C. for 3.0 h. After cooling to room temperature, water (10 mL) was added and the mixture was extracted with EtOAc (15 mL×3). The organic layers were combined, washed with brine (15 mL), dried and concentrated to yield the crude product, which was purified on Pre-HPLC to yield 8 mg of 7,8,9,10-tetrahydrocyclopenta[5,6]pyrido[4,3,2-de]phthalazin-3(2H)-one. $^1$H NMR (DMSO-d$_6$) δ 11.5 (s, 1H), 10.7 (s, 1H), 7.57 (dd, 1H, J=7.2, 7.8 Hz), 7.44 (dd, 1H, J=7.8, 1.2 Hz), 7.24 (dd, 1H, J=7.2, 1.2), 2.71-2.73 (m, 2H), 2.47-2.54 (m, 2H), and 2.01-2.03 (m, 2H). MS (ESI) m/e [M+1]$^+$ 226.0.

Example 11

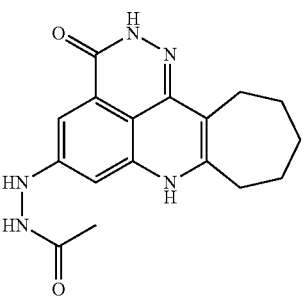 [SMILES: CC(=O)NNc1cc2c3c(n[nH]c(=O)c3c1)C1=C(CCCCC1)N2]

Step 1: Methyl 3-amino-5-fluorobenzoate

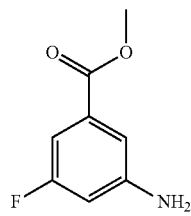

To a 3 liter round bottom flask was charged with 500 ml H$_2$SO$_4$. Fuming nitric acid was added (40 mL) and the mixture gently stirred. 2-Bromo-5-fluorobenzoic acid (60 g, 219 mmol) was added in 5 g portions over 90 minutes at 5-10° C. The mixture was stirred for 60 minutes at which time the reaction was completed. The mixture was poured into 1 liter of an ice/water mixture and extracted with EtOAc (3×600 mL). The combined organic extracts are dried (MgSO4) and concentrated under reduced pressure to give a yellow solid. The solid was suspended in hexanes and stirred for 30 minutes. The solid was collected on filter to provide 2-bromo-5-fluoro-3-nitrobenzoic acid as yellow solid (35 g, 49%).

To the solution of 2-bromo-5-fluoro-3-nitrobenzoic acid (35 g) in MeOH (400 mL) was added SOCl$_2$ (40 mL) dropwise at 10-15° C. The reaction was then stirred at 65° C. for 1 h. After cooling to room temperature, the solvent was evaporated in vacuum to afford a residue, which was chromatographed on silica gel using gradient eluant of 0-100% EtOAc in hexane to provide methyl 2-bromo-5-fluoro-3-nitrobenzoate (20 g, 84%).

To a solution of 2-bromo-5-fluoro-3-nitrobenzoate (20 g, 278 mmol) in EtOH/CH$_3$COOH (200 mL/200 mL) was added iron powder (25 g, 55 mmol). The mixture was vigorously stirred and heated to 85° C. for 1 h. After cooling, the mixture was diluted with water and basified with NaHCO$_3$ (PH=8), extracted with ethyl acetate (450 ml×3). The combined organic layer was washed with brine (500 ml), dried over MgSO4, filtered, and evaporated in vacuum. The residue was applied to flash column chromatography (silica gel) to give methyl 3-amino-2-bromo-5-fluorobenzoate (15.6 g, 87%) as red oil.

To a solution of 3-amino-2-bromo-5-fluorobenzoate (2.48 g, 10 mmol) in MeOH (80 mL) was added Pd/C (0.5 g, 5%, 50% water), the mixture was stirred at atmosphere of hydrogen for about 6.0 h. Then the mixture was filtered, washed with MeOH (10 mL). The filtrate was concentrated and recrystallized with MeOH (2.5 mL) to afford methyl 3-amino-5-fluorobenzoate (1.48 g, 88%) as a brown solid. $^1$H NMR (DMSO-d$_6$) δ 7.04 (t, 1H, J=1.8 Hz), 6.74-6.76 (m, 1H), 6.55-6.80 (m, 1H), 6.58 (m, 1H), 3.82 (s, 3H).

Step 2: Methyl 3-fluoro-11-oxo-6,7,8,9,10,11-hexahydro-5H-cyclohepta[b]quinoline-1-carboxylate

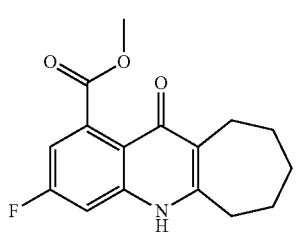 [SMILES: COC(=O)c1cc(F)cc2[nH]c3c(c(=O)c12)CCCCC3]

A mixture of methyl 2-oxocycloheptanecarboxylate (0.34 g, 2 mmol), methyl 3-amino-5-fluorobenzoate (0.33 g, 2 mmol), polyphosphoric acid (4.0 g) and dioxane (5 mL) was heated at 130° C. for 5 hours. After cooling to room temperature, the solution was diluted with water (100 mL), and NaOAc.3H$_2$O (7.3 g) was added. Then the resulting precipitate was collected by filtration and dried. The solid was suspended in methanol (20 mL) and SOCl$_2$ (10 mL) was added, the mixture was stirred at reflux for 5 hours, concentrated and treated with water (50 mL), extracted with ethyl acetate (3×50 mL). The organic layer was separated, concentrated and the residue was chromatographed to give the crude product (0.62 g). MS (ESI) m/e [M+1]$^+$290.0.

Step 3: N'-(3-oxo-2,3,7,8,9,10,11,12-octahydrocyclohepta[5,6]pyrido[4,3,2-de]phthalazin-5-yl)acetohydrazide

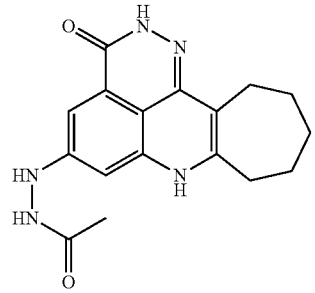

A solution of Methyl 3-fluoro-11-oxo-6,7,8,9,10,11-hexahydro-5H-cyclohepta[b]quinoline-1-carboxylate (80 mg, 0.27 mmol) and hydrazine hydrate (1.5 mL) in DMA (1.5 mL) was heated at 130° C. for 4.0 h. DMA (6 mL) and acetic acid (3 mL) were then added, and the mixture was stirred at 130° C. for another 4 hours. The reaction mixture was cooled to room temperature, then water (30 mL) was added. The mixture was extracted with EtOAc (20 mL×8). The combined organic layers were washed with aqueous NaHCO$_3$ (4×5 ml) and brine (20 ml×3), dried with Na$_2$SO$_4$ and filtered. The organic phase was concentrated in vacuum to give the crude product, which was then recrystallized from MeOH to give the product (2 mg) as a yellow solid. $^1$H NMR (DMSO-d$_6$) δ 11.4 (s, 1H), 10.0 (s, 1H), 9.78 (d, 1H, J=1.8 Hz), 8.31 (d, 1H, J=1.8 Hz), 6.77 (d, 1H, J=2.4 Hz), 6.54 (d, 1H, J=2.4 Hz), 3.17-3.31 (m, 4H), 1.77-1.78 (m, 2H), 1.59-1.61 (m, 2H), and 1.45-1.46 (m, 2H). MS (ESI) m/e [M+1]$^+$326.0.

Example 12

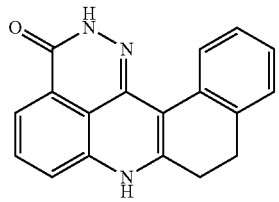 [SMILES: O=c1[nH]nc2c3c(cccc13)NC1=C2c2ccccc2CC1]

Step 1: Diethyl 3-nitrophthalate and dimethyl 3-nitrophthalate

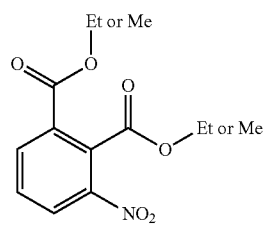

3-Nitrophthalic acid (10.0 g, 0.047 mol) was dissolved in methanol (200 mL), SOCl$_2$ (30 mL) was added dropwise during 1 hour at 0° C. The mixture was heated to reflux for 8 hours and concentrated, then treated with DMF (200 mL), K₂CO₃ (39.0 g, 0.284 mol), and iodoethane (29.0 g, 0.19 mol). Then the mixture was heated to 80° C. for 8 hours. After cooling to room temperature, the mixture was diluted with ethyl acetate (500 mL) and filtered. The filtrate was washed with water (3×300 ml) and brine (3×300 ml), dried over Na₂SO₄, filtered, and concentrated to give the mixture as a light brown solid (12.0 g, crude yield about 100%).

Step 2: Diethyl 3-aminophthalate and dimethyl 3-aminophthalate

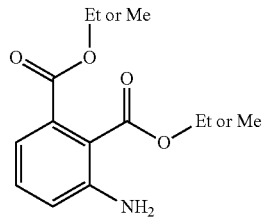

A mixture of diethyl 3-nitrophthalate and dimethyl 3-nitrophthalate (12.0 g, 47 mmol), Pd/C (5% Pd on carbon, 50% water, 2.5 g), and methanol (200 mL) was stirred at room temperature under an atmosphere of hydrogen for 5 hours. The mixture was filtered through celite and the filtrate was concentrated to give a mixture of diethyl 3-aminophthalate and dimethyl 3-aminophthalate as light yellow oil (10.0 g, crude yield 94%). The ratio of dimethyl ester vs diethyl ester was estimated as 2:3: ¹H NMR (CDC₃-d1) δ 7.23-7.24 (m, 1H), 6.88-6.91 (m, 1H), 6.78-6.80 (m, 1H), 4.30-4.34 (m, 2.5H), 3.0 (s, 1.1H), 2.90 (s, 1.2H), 1.34-1.37 (m, 3.8H).

Step 3: 12-Oxo-5,6,7,12-tetrahydrobenzo[a]acridine-11-carboxylic acid

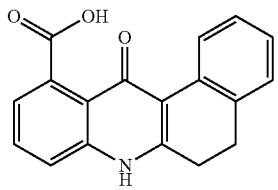 [SMILES: O=C(O)c1cccc2[nH]c3c(c(=O)c12)-c1ccccc1CC3]

A mixture of diethyl 3-aminophthalate and dimethyl 3-aminophthalate (1.0 g, 3.82 mmol), 3,4-dihydronaphthalen-2(1H)-one (0.61 g, 4.2 mmol), and aluminum trichloride (0.51 g, 3.82 mmol) was placed in a sealed tube and heated to 80° C. for 1 hour and then 130° C. for additional 4 hours. The mixture was cooled to room temperature, treated with methanol and concentrated. The remaining residue was chromatographed on silica gel using eluant of 3.2% methanol in dichloromethane and then purified by recrystalization in ethyl acetate and methanol to give the product (0.36 g, 30%) as a light brown solid. MS (ESI) m/e [M+1]⁺292.

Step 4: Methyl 12-methoxy-5,6-dihydrobenzo[a]acridine-11-carboxylate

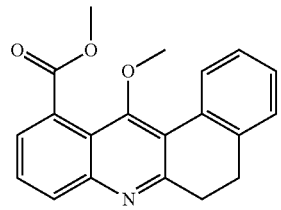 [SMILES: COC(=O)c1cccc2nc3c(c(OC)c12)-c1ccccc1CC3]

A mixture of 12-Oxo-5,6,7,12-tetrahydrobenzo[a]acridine-11-carboxylic acid (0.100 g, 0.34 mmol), K₂CO₃ (0.234 g, 1.7 mol), iodomethane (0.195 g, 1.37 mol), and DMF (1 mL) was stirred at room temperature for 16 hours, diluted with ethyl acetate (30 mL). The resulting mixture was washed with brine (6×5 ml), dried over Na₂SO₄, filtered, and concentrated. The remaining residue was chromatographed on silica gel using gradient eluant of 0-30% ethyl acetate in petroleum ether to give methyl 12-methoxy-5,6-dihydrobenzo[a]acridine-11-carboxylate as a light brown solid (20 mg, 56%). ¹H NMR (CDC₃-d1) δ8.24-8.25 (m, 1H), 8.04-8.06 (m, 1H), 7.76-7.79 (m, 1H), 7.53-7.54 (m, 1H), 7.36-7.40 (m, 3H), 4.03 (s, 3H), 3.66 (s, 3H), 3.16-3.18 (m, 2H), 3.03-3.06 (m, 2H). MS (ESI) m/e [M+1]⁺320.

Step 5: 8,9-Dihydro-2H-benzo[a]pyridazino[5,4,3-kl]acridin-3(7H)-one

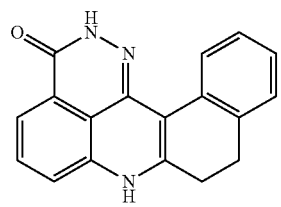 [SMILES: O=c1[nH]nc2c3c(cccc13)NC1=C2c2ccccc2CC1]

A mixture of methyl 12-methoxy-5,6-dihydrobenzo[a]acridine-11-carboxylate (20 mg, 0.06 mmol) and hydrazine hydrate (0.5 mL) in DMA (0.8 mL) was heated at 130° C. for 4 h. The reaction mixture was cooled, treated with ethyl acetate (0.5 mL), water (1 mL) and brine (1 mL). The resulting precipitate was collected by filtration, dissolved in a mixture of methanol:dichloromethane (1:8, 10 mL), dried over Na₂SO₄, filtered, concentrated, chromatographed on silica gel using gradint eluant of 0-3.2% methanol in dichloromethane to give the desired compound as a yellow solid (7 mg, 39%). ¹H NMR (DMSO-d₆) δ11.85 (s, 1H), 10.88 (s, 1H), 8.77-8.78 (m, 1H), 7.66-7.68 (m, 1H), 7.56-7.57 (m, 1H), 7.35-7.37 (m, 1H), 7.19-7.20 (m, 2H), 7.09-7.11 (m, 1H), 2.83-2.85 (m, 2H), 2.66-2.69 (m, 2H). MS (ESI) m/e [M+1]⁺288.

Example 13

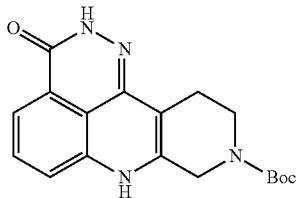 [SMILES: CC(C)(C)OC(=O)N1CCC2=C(C1)Nc1cccc3c(=O)[nH]nc2c13]

Step 1: Methyl 2-benzyl-9-bromo-5-oxo-1,2,3,4,5,10-hexahydrobenzo[b][1,7]naphthyridine-6-carboxylate

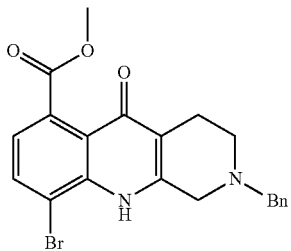 [SMILES: COC(=O)c1ccc(Br)c2[nH]c3c(c(=O)c12)CCN(Cc1ccccc1)C3]

A mixture of ethyl 1-benzyl-3-oxopiperidine-4-carboxylate (16.1 g, 70 mmol), methyl 3-amino-4-bromobenzoate (21.9 g, 84 mmol), polyphosphoric acid (120 g) and dioxane (120 mL) was heated at 110° C. for 4 hours. After cooling to room temperature, the mixture was poured into ice water, filtered and the filtrate was extracted with EtOAc (500 mL×3). The combined organic layers were dried, and concentrated to give crude residue, which was chromatographed on silica gel using gradient eluant of 20% to 50% ethyl acetate in petroleum ether to give the crude product. Then the crude product was dissolved in MeOH (1 L), TMSCl (150 mL) was added, and the mixture was stirred at reflux for 12 h. After cooling to room temperature, the solvent was evaporated and the residue was recrystallized from MeOH to afford methyl 2-benzyl-9-bromo-5-oxo-1,2,3,4,5,10-hexahydrobenzo[b][1,7]naphthyridine-6-carboxylate (7.6 g). $^1$H NMR (CDC$_3$-d1) δ 10.9 (s, 1H), 8.06 (d, 1H, J=7.8 Hz), 7.51-7.74 (m, 5H), 7.20 (d, 1H, J=7.8 Hz), 4.36-4.62 (m, 4H), 3.82 (s, 3H), 3.67-3.72 (m, 2H), and 2.82-2.83 (m, 2H). MS (ESI) m/e [M+1]$^+$427.0.

Step 2: Methyl 5-oxo-1,2,3,4,5,10-hexahydrobenzo[b][1,7]naphthyridine-6-carboxylate hydrobromide

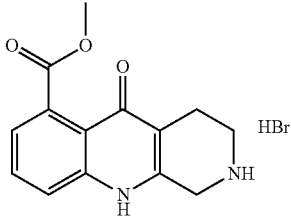 [SMILES: COC(=O)c1cccc2[nH]c3c(c(=O)c12)CCNC3 ; Br]

To a solution of methyl 2-benzyl-9-bromo-5-oxo-1,2,3,4,5,10-hexahydrobenzo[b][1,7]naphthyridine-6-carboxylate (6.6 g, 15.4 mmol) in MeOH (100 mL) was added Pd/C (3.0 g, 5%, 50% water), the mixture was stirred at atmosphere of hydrogen for about 6.0 h. Then the mixture was filtered, washed with MeOH (20 mL). The filtrate was concentrated and the residue was recrystallized with MeOH (2.5 mL) to afford the product (3.4 g, 65%) as a white solid. $^1$H NMR (DMSO-d$_6$) δ 12.0 (s, 1H), 9.18 (s, 1H), 7.61-7.72 (m, 2H), 7.22-7.23 (m, 1H), 4.32 (s, 2H), 3.81 (s, 3H), 3.38-3.40 (m, 2H), and 2.66-2.67 (m, 2H).

Step 3: Tert-butyl 3-oxo-7,8,10,11-tetrahydro-2H-phthalazino[8,1-bc][1,7]naphthyridine-9(3H)-carboxylate

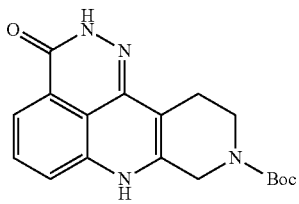 [SMILES: CC(C)(C)OC(=O)N1CCC2=C(C1)Nc1cccc3c(=O)[nH]nc2c13]

To a solution of methyl 5-oxo-1,2,3,4,5,10-hexahydrobenzo[b][1,7]naphthyridine-6-carboxylate hydrobromide (310 mg, 0.9 mmol) in dioxane (30 mL) were added (Boc)20 (375 mg, 1.72 mmol) and Et$_3$N (5 mL), the mixture was then stirred at room temperature for 0.5 h. The reaction was quenched with aqueous NaHCO$_3$ (15 mL), and the mixture was extracted with EtOAc (25 mL×3). The combined organic layer was washed with water (20 mL) and brine (20 mL), dried and concentrated to give crude 2-tert-butyl 6-methyl 5-oxo-3,4,5,10-tetrahydrobenzo[b][1,7]naphthyridine-2,6(1H)-dicarboxylate (0.55 g), which was used for the next step without further purified. $^1$H NMR (DMSO-d$_6$) δ 11.8 (s, 1H), 7.54-7.66 (m, 2H), 7.16-7.17 (m, 1H), 4.12 (s, 2H), 3.80 (s, 3H), 3.57-3.80 (m, 2H), 3.56-3.58 (m, 2H), and 1.48 (s, 9H).

A solution of 2-tert-butyl 6-methyl 5-oxo-3,4,5,10-tetrahydrobenzo[b][1,7]naphthyridine-2,6(1H)-dicarboxylate (0.55 g) and hydrazine hydrate (2.5 mL) in DMA (4 mL) was heated at 130° C. for 2.0 h, acetic acid (4 mL) was added and the mixture was stirred at 130° C. for another 6 hours. The reaction mixture was cooled to room temperature, then water (30 mL) and EtOAc (100 mL) were added. The organic phase was separated and then washed with aqueous NaHCO$_3$ (2×10 ml) and brine (20 ml), dried with Na$_2$SO$_4$ and filtered. The organic phase was concentrated in vacuum to give the crude product, which was then recrystallized from MeOH to afford the product (110 mg, 21%) as a yellow solid. $^1$H NMR (DMSO-d$_6$) δ 11.7 (s, 1H), 10.52 (s, 1H), 7.60 (t, 1H, J=8.0 Hz), 7.43 (d, 1H, J=8.0 Hz), 7.21 (d, 1H, J=8.0 Hz), 4.22 (s, 2H), 3.54-3.55 (m, 2H), 2.30-2.33 (m, 2H), and 1.40 (s, 9H). MS (ESI) m/e [M+1]$^+$341.0.

Example 14

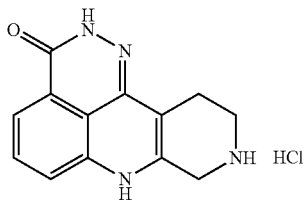 [SMILES: O=c1[nH]nc2c3c(cccc13)NC1=C2CCNC1 ; Cl]

8,9,10,11-Tetrahydro-2H-phthalazino[8,1-bc][1,7]naphthyridin-3 (7H)-one

To a solution of tert-butyl 3-oxo-7,8,10,11-tetrahydro-2H-phthalazino[8,1-bc][1,7]naphthyridine-9(3H)-carboxylate (100 mg) in dioxane (6 mL) was added con.HCl (2.0 mL) dropwise, the mixture was then stirred at room temperature for 0.5 h. The solvent was evaporated in vacuo and water (10 mL) was added. The mixture was washed with methylene dichloride (20 mL), and the aqueous phase was evaporated to afford 8,9,10,11-tetrahydro-2H-phthalazino[8,1-bc][1,7]naphthyridin-3(7H)-one hydrochloride (46 mg, 57%). $^1$H NMR (DMSO-d$_6$) δ 11.9 (s, 1H), 10.95 (s, 1H), 9.59 (s, 1H), 7.34-7.69 (m, 3H), 3.33-3.51 (m, 4H), 2.55-2.56 (m, 2H). MS (ESI) m/e [M+1]$^+$241.0.

Example 15

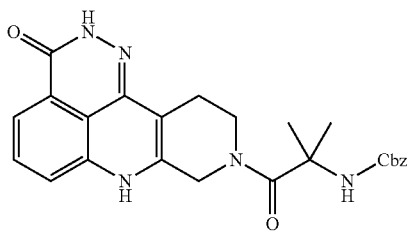 [SMILES: CC(C)(NC(=O)OCc1ccccc1)C(=O)N1CCC2=C(C1)Nc1cccc3c(=O)[nH]nc2c13]

Step 1: Methyl 2-(2-(((benzyloxy)carbonyl)amino)-2-methylpropanoyl)-5-oxo-1,2,3,4,5,10-hexahydrobenzo[b][1,7]naphthyridine-6-carboxylate

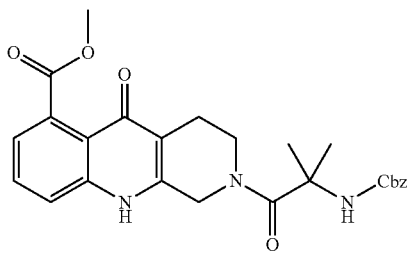 [SMILES: COC(=O)c1cccc2[nH]c3c(c(=O)c12)CCN(C(=O)C(C)(C)NC(=O)OCc1ccccc1)C3]

To a solution of 2-(((benzyloxy)carbonyl)amino)-2-methylpropanoic acid (385 mg, 1.62 mmol) in DMF (8.0 mL) were added HATU (1.1 g, 2.94 mmol), DIPEA (0.75 g, 5.87 mmol), and methyl 5-oxo-1,2,3,4,5,10-hexahydrobenzo[b][1,7]naphthyridine-6-carboxylate hydrobromide (410 mg, 1.6 mmol). The mixture was then stirred at room temperature for 24 h. Then the reaction was quenched by water (20 mL). The mixture was extracted with THF/EtOAc (10 ml/60 ml) three times. The organic layers were combined, dried, concentrated, and chromatographed on silica gel using gradient eluant of 0-50% methanol in dichloromethane to give the desired compound as pale solid (114 mg, 14%). MS (ESI) m/e [M+1]$^+$478.

Step 2: Benzyl(2-methyl-1-oxo-1-(3-oxo-10,11-dihydro-2H-phthalazino[8,1-bc][1,7]naphthyridin-9(3H,7H,8H)-yl)propan-2-yl)carbamate

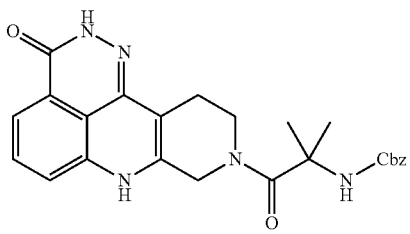 [SMILES: CC(C)(NC(=O)OCc1ccccc1)C(=O)N1CCC2=C(C1)Nc1cccc3c(=O)[nH]nc2c13]

A solution of methyl 2-(2-(((benzyloxy)carbonyl)amino)-2-methylpropanoyl)-5-oxo-1,2,3,4,5,10-hexahydrobenzo[b][1,7]naphthyridine-6-carboxylate (0.11 g) and hydrazine hydrate (1.0 mL) in DMA (1.5 mL) was heated at 130° C. for 1.5 h, acetic acid (2.0 mL) was added and the mixture was stirred at 130° C. for another 12 hours. The reaction mixture was cooled to room temperature, then water (15 mL) and EtOAc (50 mL) were added. The organic phase was separated and then washed with aqueous NaHCO$_3$ (2×10 ml) and brine (20 ml), dried over Na$_2$SO$_4$, filtered, the organic phase was concentrated in vacuum to give the crude product, which was purified by Pre-HPLC to afford benzyl (2-methyl-1-oxo-1-(3-oxo-10,11-dihydro-2H-phthalazino[8,1-bc][1,7]naphthyridin-9(3H,7H,8H)-yl)propan-2-yl)carbamate (46 mg, 42%) as a yellow solid. $^1$H NMR (DMSO-d$_6$) δ 11.8 (s, 1H), 10.6 (s, 1H), 8.4 (s, 1H), 7.65 (t, 1H, J=7.8 Hz), 7.49 (d, 1H, J=7.8 Hz), 7.25-7.35 (m, 6H), 4.90-4.91 (m, 2H), 4.34-4.40 (m, 2H), 3.83-3.89 (m 2H), 2.32-2.34 (m, 2H), and 1.40 (s, 6H). MS (ESI) m/e [M+1]$^+$460.0.

Example 16

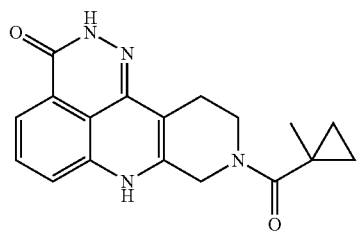 [SMILES: CC1(C(=O)N2CCC3=C(C2)Nc2cccc4c(=O)[nH]nc3c24)CC1]

Step 1: Methyl 2-(1-methylcyclopropanecarbonyl)-5-oxo-1,2,3,4,5,10-hexahydrobenzo[b][1,7]naphthyridine-6-carboxylate

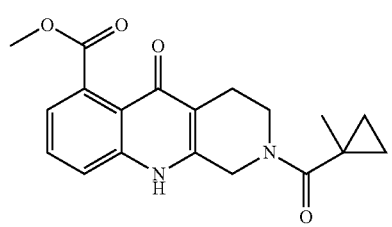 [SMILES: COC(=O)c1cccc2[nH]c3c(c(=O)c12)CCN(C(=O)C1(C)CC1)C3]

A solution of HATU (340 mg, 0.9 mmol) in DMF (2 ml) was added to a mixture of methyl 5-oxo-1,2,3,4,5,10-hexahydrobenzo[b][1,7]naphthyridine-6-carboxylate (200 mg, 0.77 mmol) from Example 13 (Step 2), 1-methylcyclopropanecarboxylic acid (102 mg, 1.02 mmol), diisopropylethylamine (0.5 mL, 5.09 mmol) and DMF (8 ml). The resultant mixture was stirred at ambient temperature for 8 hours. The DMF was evaporated and the residue was purified by pre-TLC to give methyl 2-(1-methylcyclopropanecarbonyl)-5-oxo-1,2,3,4,5,10-hexahydrobenzo[b][1,7]naphthyridine-6-carboxylate (65 mg, 25%) as yellow solid.

Step 2: 9-(1-Methylcyclopropanecarbonyl)-8,9,10,11-tetrahydro-2H-phthalazino[8,1-bc][1,7]naphthyridin-3(7H)-one

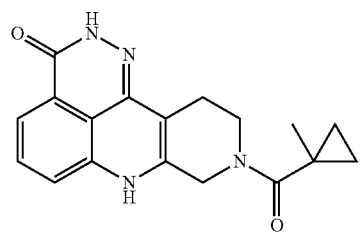 [SMILES: CC1(C(=O)N2CCC3=C(C2)Nc2cccc4c(=O)[nH]nc3c24)CC1]

The target product was prepared from methyl 2-(1-methylcyclopropanecarbonyl)-5-oxo-1,2,3,4,5,10-hexahydrobenzo[b][1,7]naphthyridine-6-carboxylate and hydrazine hydrate according to the same procedure described as in Example 1 (step 4). 1H NMR (DMSO-d6) δ 11.8 (s, 1H), 10.6 (s, 1H), 7.62-7.64 (m, 1H), 7.47-7.49 (m, 1H), 7.24-7.26 (m, 1H), 4.41 (bs, 2H), 3.85 (bs, 2H), 2.42 (bs, 2H), 1.28 (s, 3H), 0.84 (bs, 2H), 0.60 (bs, 2H). MS (ESI) m/e [M+1]+323.

Example 17

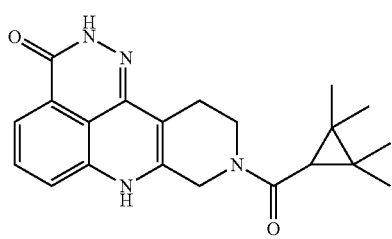 [SMILES: CC1(C)C(C(=O)N2CCC3=C(C2)Nc2cccc4c(=O)[nH]nc3c24)C1(C)C]

Step 1: Methyl 5-oxo-2-(2,2,3,3-tetramethylcyclopropanecarbonyl)-1,2,3,4,5,10-hexahydrobenzo[b][1,7]naphthyridine-6-carboxylate

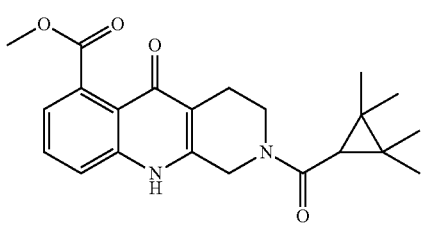

The product was prepared from methyl 5-oxo-1,2,3,4,5,10-hexahydrobenzo[b][1,7]naphthyridine-6-carboxylate and 2,2,3,3-tetramethyl cyclopropanecarboxylic acid according to the same procedure described as in Example 16 (step 1)

Step 2: 9-(2,2,3,3-Tetramethylcyclopropanecarbonyl)-8,9,10,11-tetrahydro-2H-phthalazino[8,1-bc][1,7]naphthyridin-3(7H)-one

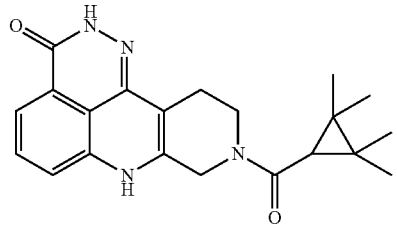 [SMILES: CC1(C)C(C(=O)N2CCC3=C(C2)Nc2cccc4c(=O)[nH]nc3c24)C1(C)C]

The target product was prepared from methyl 5-oxo-2-(2,2,3,3-tetramethylcyclopropanecarbonyl)-1,2,3,4,5,10-hexahydrobenzo[b][1,7]naphthyridine-6-carboxylate and hydrazine hydrate according to the same procedure described as in Example 16 (Step 4). $^1$H NMR (DMSO-d$_6$) δ 11.8 (s, 1H), 10.6-10.65 (m, 1H), 7.62-7.67 (m, 1H), 7.47-7.48 (m, 1H), 7.24-7.31 (m, 1H), 4.36-4.41 (m, 2H), 3.70-3.76 (m, 2H), 2.29-2.33 (m, 2H), 1.03-1.23 (m, 12H). MS (ESI) m/e [M+1]+ 369.

Example 18

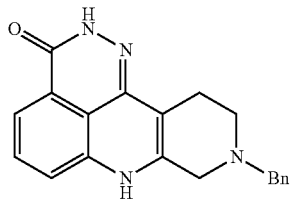 [SMILES: O=c1[nH]nc2c3c(cccc13)NC1=C2CCN(Cc2ccccc2)C1]

Step 1: Methyl 2-benzyl-5-oxo-1,2,3,4,5,10-hexahydrobenzo[b][1,7]naphthyridine-6-carboxylate

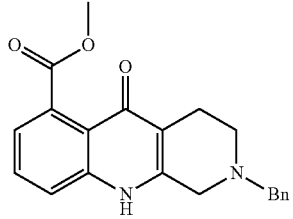 [SMILES: COC(=O)c1cccc2[nH]c3c(c(=O)c12)CCN(Cc1ccccc1)C3]

To a solution of methyl 2-benzyl-9-bromo-5-oxo-1,2,3,4,5,10-hexahydrobenzo[b][1,7]naphthyridine-6-carboxylate (0.1 g, 0.23 mmol) in MeOH (3 mL) was added Pd/C (0.04 g, 5%, 50% water), and the mixture was stirred at atmosphere of hydrogen for about 2.5 h. Debromination occurred without substantially removing benzyl group under this condition. Then the mixture was filtered, washed with MeOH (50 mL), concentrated and was chromatographed on silica gel to afford the product (0.05 g). MS (ESI) m/e [M+1]+ 349.0.

Step 2: 9-benzyl-8,9,10,11-tetrahydro-2H-phthalazino[8,1-bc][1,7]naphthyridin-3(7H)-one

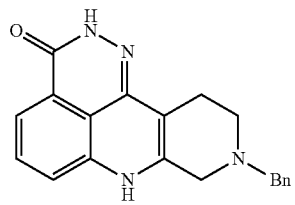 [SMILES: O=c1[nH]nc2c3c(cccc13)NC1=C2CCN(Cc2ccccc2)C1]

Example 18 was prepared from methyl 2-benzyl-5-oxo-1,2,3,4,5,10-hexahydrobenzo[b][1,7]naphthyridine-6-carboxylate and hydrazine hydrate according to the same procedures described as those in Example 15. $^1$H NMR (DMSO-$d_6$) δ 8.37 (s, 1H), 7.21-7.56 (m, 8H), 3.81 (s, 2H), 3.39 (s, 2H), 2.91 (t, 2H, J=8.4 Hz), and 2.25 (t, 2H, J=8.4 Hz). MS (ESI) m/e [M+1]$^+$ 331.0.

Biological Activity

PARP-1 Enzymatic Assay

PARP1 enzymatic assay was conducted using a method modified from HT F Homogeneous PARP Inhibition Assay Kit (Trevigen). 8.8 nM PARP1 was pre-incubated with different concentrations of compounds in a buffer containing 100 mM Tris-HCl pH 8.0, 100 mM NaCl, 20 mM $MgCl_2$, and 1% DMSO for 30 min at RT. The auto-PARsylation reaction was initiated by addition of 500 nM NAD and 20 ng/ul activated DNA (Sigma) and incubated at RT for 40 min. The remaining NAD was detected by incubation with cycling assay solution containing 1% ethanol, 0.30 U/ml alcohol dehydrogenase, 25 uM resazurin, and 0.25 U/ml diaphorase for 50 min at RT. The concentration of NAD is proportional to the fluorescence signal at Ex540 nm/Em 590 nm. The $IC_{50}$s were calculated based on residual enzyme activity (the rate of NAD decrease) in presence of increasing concentrations of compounds.

PARP-2 and PARP-3 Enzymatic Assay

PARP2 and PARP3 enzymatic assays were conducted using commercial PARP-2/PARP-3 Chemiluminescent Assay Kit (BPS Biosciences) and the protocols with the kits. Briefly, histones were coated in a high binding plate first, and incubated with PARP-2 or PARP-3, and increasing concentrations of compounds for 0.5 h. Then, biotinylated NAD and activated DNA were added to the wells. The biotinylated PARsylation product was measured by adding streptavidin-HRP and HRP substrates which produce chemiluminescence. The $IC_{50}$s were calculated based on residual enzyme activity in presence of increasing concentrations of compounds.

Tankyrase-2 Enzymatic Assay

Tankyrase-2 enzymatic assay was conducted using commercial Tankyrase-2 Chemiluminescent Assay Kit (BPS Biosciences) and the protocol with the kit. GST-fused tankyrase-2 (recombinant protein expressed and purified from Bacluovirus) were coated on a GSH-precoated plate first, and incubated with increasing concentrations of compounds for 0.5 h. Then, biotinylated NAD was added to the wells. The biotinylated auto-PARsylation product was measured by adding streptavidin-HRP and HRP substrates which produce chemiluminescence. The $IC_{50}$s were calculated based on residual enzyme activity in presence of increasing concentrations of compounds.

PARylation Assay.

HeLa cells were seeded into a 96-well plate with clear bottom and black wall at an initial concentration of 5000 cells/well in culture medium (100 μL of DMEM containing 10% FBS, 0.1 mg/mL penicillin-streptomycin, and 2 mML-glutamine). The plates were incubated for 4 h at 37° C. under 5% $CO_2$ atmosphere, and then compounds were added with serial dilutions over eight points over a 0.01 nM-10 μM final concentration range in 0.1% DMSO/culture medium. The plate was then incubated for 18 h at 37° C. in 5% $CO_2$. Then DNA damage was provoked by addition of 60 μL of $H_2O_2$ solution in PBS (final concentration 200 μM). As a negative control, cells untreated with $H_2O_2$ were used. The plate was kept at 37° C. for 5 min. Then the medium was gently removed by plate inversion, and the cells were fixed by addition of ice-cold MeOH (100 μL/well) and kept at −20° C. for 20 min. After removal of the fixative by plate inversion and washing 10 times with PBS (120 μL), the detection buffer (50 μL/well, containing PBS, Tween (0.1%), and BSA (1 mg/mL)) together with the primary PAR mAb (Alexis ALX-804-220, 1:2000), the secondary anti-mouse Alexa Fluor 488 antibody (MolecularProbes A11029, 1:2000), and nuclear dye DAPI (Molecular Probes D3571, 150 nM) were added. Following overnight incubation at 4° C. in the dark, removal of the solution, and washing 6 times with PBS (120 μL), the plate was read on an ArrayScan VTI (ThermoFisher). Monitoring for PAR polymer was by detection of Alexa488 at XF100_485_20, exposure time of 0.05 s, and identification of the nuclei was by tracking DAPI with XF100_386_23, exposure time of 0.01 s. The mean value of total intensity of cells was calculated by measuring the average of total intensity of nuclei over the total number of DAPI-labeled nuclei. The EC50 was determined on the basis of the residual enzyme activity in the presence of increasing PARPi concentration.

Examples 1-18 as disclosed herein were tested and found to inhibit PARP, such as PARP-1, PARP-2, PARP-3, and Tankyrase-2, with $IC_{50}$ values ranging from subnanomolar to 10 micromolar.

TABLE 2

| | $IC_{50}$s and $EC_{50}$s (nM) | | | | |
|---|---|---|---|---|---|
| Example | PARP-1 $IC_{50}$ | PARP-2 $IC_{50}$ | PARP-3 $IC_{50}$ | Tankyrase-2 $IC_{50}$ | PARP PARylation EC50 |
| 1 | 6.3 | 0.7 | 18 | 15.6 | 0.8 |

TABLE 2-continued
| | IC$_{50}$s and EC$_{50}$s (nM) | | | | |
|---|---|---|---|---|---|
| Example | PARP-1 IC$_{50}$ | PARP-2 IC$_{50}$ | PARP-3 IC$_{50}$ | Tankyrase-2 IC$_{50}$ | PARP PARylation EC50 |
| 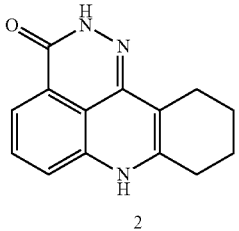 [SMILES: O=c1[nH]nc2c3c(cccc13)NC1=C2CCCC1] 2 | 6.1 | 0.77 | | 3.2 | 1.2 |
| 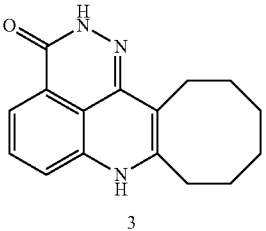 [SMILES: O=c1[nH]nc2c3c(cccc13)NC1=C2CCCCCC1] 3 | 5.9 | 0.73 | 25 | 15 | 0.6 |
| 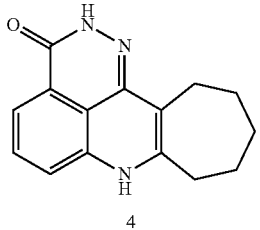 [SMILES: O=c1[nH]nc2c3c(cccc13)NC1=C2CCCCC1] 4 | 4.9 | 0.9 | 30.3 | 15.4 | 0.75 |
| 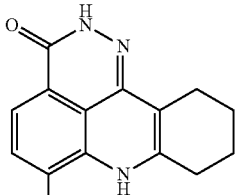 5 | 70.7 | | | | 477 |
| 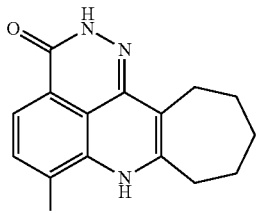 6 | 67 | | | | 139 |

TABLE 2-continued
| Example | PARP-1 IC$_{50}$ | PARP-2 IC$_{50}$ | PARP-3 IC$_{50}$ | Tankyrase-2 IC$_{50}$ | PARP PARylation EC50 |
|---|---|---|---|---|---|
| 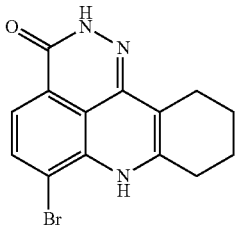 7 | 17 | | | | 32 |
| 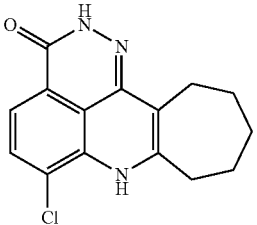 8 | 52.5 | | | 2.3% Inhibition @ 50 nM | 43.2 |
| 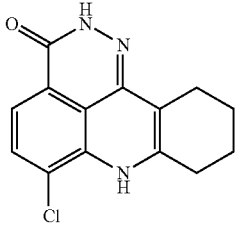 9 | 10.3 | | | 14.1% @ 50 nM | 43.2 |
| 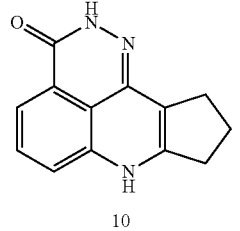 [SMILES: O=c1[nH]nc2c3c(cccc13)NC1=C2CCC1] 10 | 6.0 | | | 17.5 | 4.6 |
| 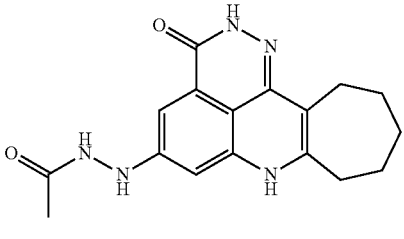 11 | 59 | | | | |
IC$_{50}$s and EC$_{50}$s (nM)

TABLE 2-continued
| | IC₅₀s and EC₅₀s (nM) | | | | |
|---|---|---|---|---|---|
| Example | PARP-1 IC$_{50}$ | PARP-2 IC$_{50}$ | PARP-3 IC$_{50}$ | Tankyrase-2 IC$_{50}$ | PARP PARylation EC50 |
| 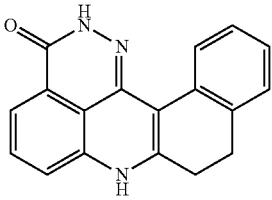 12 | 54.6 | | | 14.3% Inhibition @ 50 nM | 6.8 |
| 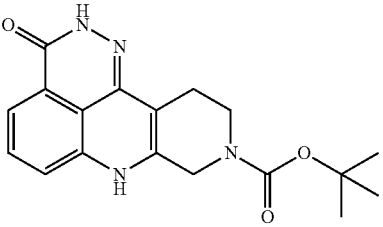 13 | 5.1 | 0.5 | 270 | 7.0 | 0.7 |
| 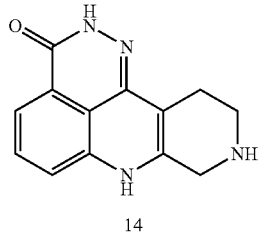 [SMILES: O=c1[nH]nc2c3c(cccc13)NC1=C2CCNC1] 14 | 7.6 | 1.2 | 18 | 120 | 14 |
| 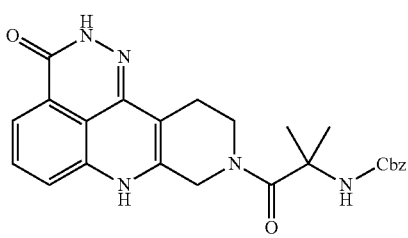 15 | 23 | | | | 269 |
| 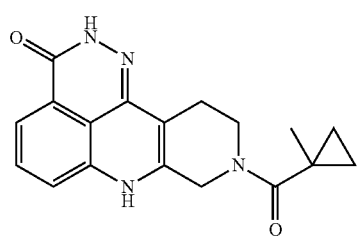 16 | 7.2 | | | | 5.4 |

TABLE 2-continued

IC$_{50}$s and EC$_{50}$s (nM)

| Example | PARP-1 IC$_{50}$ | PARP-2 IC$_{50}$ | PARP-3 IC$_{50}$ | Tankyrase-2 IC$_{50}$ | PARP PARylation EC50 |
|---|---|---|---|---|---|
| 17 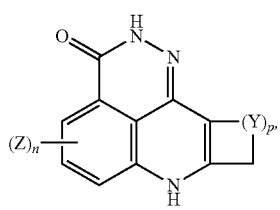 | 8.0 | | | | 0.9 |
| 18 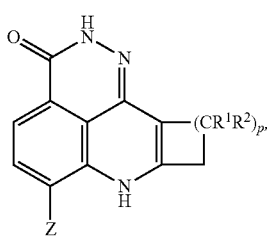 | 8.7 | 1.5 | 2000 | 43 | 9.7 |

What is claimed is:

1. A compound of Formula (I):

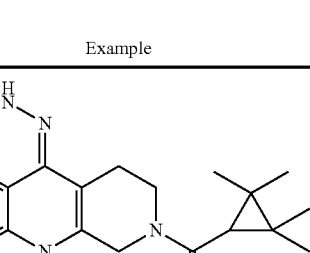

(I)

or a pharmaceutically acceptable salt thereof,
wherein:
Y, at each occurrence, is independently selected from —CR$^1$R$^2$;
p is 5;
Z, at each occurrence, is independently selected from hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent R$^9$;
n is 0, 1, 2 or 3;
R$^1$ and R$^2$, which may be the same or different, are each selected from hydrogen, halogen, alkyl, alkenyl, alkynyl, cycloalkyl, aryl, heterocyclyl, heteroaryl, —NR$^6$R$^7$, —OR$^6$, —COR$^6$, —CO$_2$R$^6$, —CONR$^6$R$^7$, —NR$^6$CONR$^7$R$^8$, —NR$^6$CO$_2$R$^7$, —NR$^6$SO$_2$R$^7$, and —SO$_2$R$^6$, wherein each of the alkyl, alkenyl, alkynyl, cycloalkyl, heteroaryl, aryl, and heterocyclyl is optionally substituted with at least one substituent R$^9$;
R$^6$, R$^7$ and R$^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent R$^9$; and
R$^9$, at each occurrence, is independently selected from halogen, haloalkyl, alkyl, alkenyl, cycloalkyl, aryl, heteroaryl, heterocyclyl, alkynyl, oxo, —CN, —OR', —NR'R'', —COR', —CO$_2$R', —CONR'R'', —C(=NR')NR''R''', —NR'COR'', —NR'CONR'R''', —NR'CO$_2$R'', —SR', —SOR', —SO$_2$R', —NR'SO$_2$NR''R''', and NR'SO$_2$R'', wherein R', R'', and R''' are independently selected from hydrogen, haloalkyl, alkyl, arylalkyl, alkenyl, alkynyl, cycloalkyl, heterocyclyl, aryl, and heteroaryl.

2. The compound of claim 1, which is a compound of Formula (II-1):

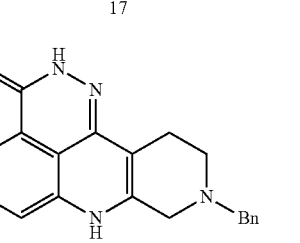

(II-1)

or a pharmaceutically acceptable salt thereof,
wherein
p is 5;
Z, is selected from hydrogen, halogen, alkyl, alkenyl, alkynyl, cycloalkyl, aryl, heterocyclyl, heteroaryl, —CN, —NO$_2$, —OR$^6$, —NR$^6$R$^7$, —NR$^6$COR$^7$, —NR$^6$—NR$^7$COR$^8$, —NR$^6$SO$_2$R$^7$, —CONR$^6$R$^7$, —COOR$^6$, and —SO$_2$R$^6$, wherein each of the alkyl, alkenyl, alkynyl, cycloalkyl, heteroaryl, aryl, and heterocyclyl is optionally substituted with at least one substituent $R^9$;

$R^1$ and $R^2$, which may be the same or different, are each selected from hydrogen, halogen, alkyl, alkenyl, alkynyl, cycloalkyl, aryl, heterocyclyl, heteroaryl, —$NR^6R^7$, —$OR^6$, —$COR^6$, —$CO_2R^6$, —$CONR^6R^7$, —$NR^6CONR^7R^8$, —$NR^6CO_2R^7$, —$NR^6SO_2R^7$, and —$SO_2R^6$, wherein each of the alkyl, alkenyl, alkynyl, cycloalkyl, heteroaryl, aryl, and heterocyclyl is optionally substituted with at least one substituent $R^9$;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$; and $R^9$, at each occurrence, is independently selected from hydrogen, halogen, haloalkyl, alkyl, alkenyl, cycloalkyl, aryl, heteroaryl, heterocyclyl, alkynyl, oxo, —CN, —OR', —NR'R", —COR', —$CO_2$R', —CONR'R", —C(=NR')NR"R''', —NR'COR", —NR'CONR'R", —NR'$CO_2$R", —SR', —SOR', —$SO_2$R', —NR'$SO_2$NR"R''', and NR'$SO_2$R", wherein R', R", and R''' are independently selected from hydrogen, haloalkyl, alkyl, arylalkyl, alkenyl, alkynyl, cycloalkyl, heterocyclyl, aryl, and heteroaryl.

3. The compound of claim 1, which is a compound of Formula (II-2):

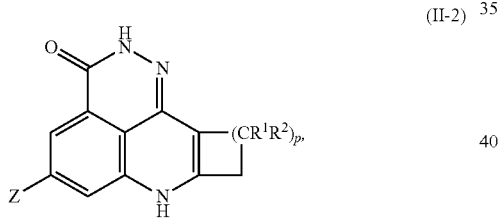

(II-2)

or a pharmaceutically acceptable salt thereof,
wherein
p is 5;

Z is selected from hydrogen, halogen, alkyl, alkenyl, alkynyl, cycloalkyl, aryl, heterocyclyl, heteroaryl, —CN, —$NO_2$, —$OR^6$, —$NR^6R^7$, —$NR^6COR^7$, —$NR^6$—$NR^7COR^8$, —$NR^6SO_2R^7$, —$CONR^6R^7$, —$COOR^6$, and —$SO_2R^6$, wherein each of the alkyl, alkenyl, alkynyl, cycloalkyl, heteroaryl, aryl, and heterocyclyl is optionally substituted with at least one substituent $R^9$;

$R^1$ and $R^2$, which may be the same or different, are each selected from hydrogen, halogen, alkyl, alkenyl, alkynyl, cycloalkyl, aryl, heterocyclyl, heteroaryl, —$NR^6R^7$, —$OR^6$, —$COR^6$, —$CO_2R^6$, —$CONR^6R^7$, —$NR^6CONR^7R^8$, —$NR^6CO_2R^7$, —$NR^6SO_2R^7$, and —$SO_2R^6$, wherein each of the alkyl, alkenyl, alkynyl, cycloalkyl, heteroaryl, aryl, and heterocyclyl is optionally substituted with at least one substituent $R^9$;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$; and $R^9$, at each occurrence, is independently selected from halogen, haloalkyl, alkyl, alkenyl, cycloalkyl, aryl, heteroaryl, heterocyclyl, alkynyl, oxo, —CN, —OR', —NR'R", —COR', —$CO_2$R', —CONR'R", —C(=NR')NR"R''', —NR'COR", —NR'CONR'R", —NR'$CO_2$R", —SR', —SOR', —$SO_2$R', —NR'$SO_2$NR"R''', and NR'$SO_2$R", wherein R', R", and R''' are independently selected from hydrogen, haloalkyl, alkyl, arylalkyl, alkenyl, alkynyl, cycloalkyl, heterocyclyl, aryl, and heteroaryl.

4. The compound of claim 1, which is a compound of Formula (II-3):

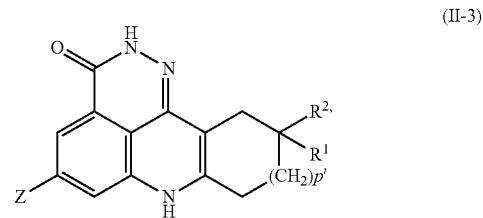

(II-3)

or a pharmaceutically acceptable salt thereof,
wherein
p' is 3;

Z is selected from the group consisting of hydrogen, halogen, alkyl, alkenyl, alkynyl, cycloalkyl, aryl, heterocyclyl, heteroaryl, —CN, —$NO_2$, —$OR^6$, —$NR^6R^7$, —$NR^6COR^7$, —$NR^6$—$NR^7COR^8$, —$NR^6SO_2R^7$, —$CONR^6R^7$, —$COOR^6$, and —$SO_2R^6$, wherein each of the alkyl, alkenyl, alkynyl, cycloalkyl, heteroaryl, aryl, and heterocyclyl is optionally substituted with at least one substituent $R^9$;

$R^1$ and $R^2$, which may be the same or different, are each selected from hydrogen, halogen, alkyl, alkenyl, alkynyl, cycloalkyl, aryl, heterocyclyl, heteroaryl, —$NR^6R^7$, —$OR^6$, —$COR^6$, —$CO_2R^6$, —$CONR^6R^7$, —$NR^6CONR^7R^8$, —$NR^6CO_2R^7$, —$NR^6SO_2R^7$, and —$SO_2R^6$, wherein each of the alkyl, alkenyl, alkynyl, cycloalkyl, heteroaryl, aryl, and heterocyclyl is optionally substituted with at least one substituent $R^9$;

$R^6$, $R^7$ and $R^8$, which may be the same or different, are each selected from hydrogen, alkyl, alkenyl, alkynyl, cycloalkyl, heterocyclyl, aryl, and heteroaryl, wherein each of the alkyl, alkenyl, alkynyl, cycloalkyl, heteroaryl, aryl, and heterocyclyl is optionally substituted by at least one substituent $R^9$; and $R^9$, at each occurrence, is independently selected from hydrogen, halogen, haloalkyl, alkyl, alkenyl, cycloalkyl, aryl, heteroaryl, heterocyclyl, alkynyl, oxo, —CN, —OR', —NR'R", —COR', —$CO_2$R', —CONR'R", —C(=NR')NR"R''', —NR'COR", —NR'CONR'R", —NR'$CO_2$R", —SR', —SOR', —$SO_2$R', —NR'$SO_2$NR"R''', and NR'$SO_2$R", wherein R', R", and R''' are independently selected from hydrogen, haloalkyl, alkyl, arylalkyl, alkenyl, alkynyl, cycloalkyl, heterocyclyl, aryl, and heteroaryl.

5. A pharmaceutical composition comprising at least one pharmaceutically acceptable carrier and as an active ingredient a therapeutically effective of the compound of claim 1, or a pharmaceutically acceptable salt thereof.
6. A compound:
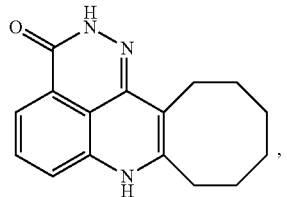 [SMILES: O=c1[nH]nc2c3c(cccc13)NC1=C2CCCCCC1]
or a pharmaceutically acceptable salt thereof.
* * * * *